US 6,780,586 B1

(12) United States Patent
Gish et al.

(10) Patent No.: US 6,780,586 B1
(45) Date of Patent: Aug. 24, 2004

(54) METHODS OF DIAGNOSING BREAST CANCER

(75) Inventors: Kurt C. Gish, San Francisco, CA (US); David Mack, Menlo Park, CA (US)

(73) Assignee: Protein Design Labs, Inc., Femont, CA (US)

( * ) Notice: Subject to any disclaimer, the term of this patent is extended or adjusted under 35 U.S.C. 154(b) by 116 days.

(21) Appl. No.: 09/702,216

(22) Filed: Oct. 30, 2000

Related U.S. Application Data

(63) Continuation-in-part of application No. 09/525,361, filed on Mar. 15, 2000, and a continuation-in-part of application No. 09/453,137, filed on Dec. 2, 1999, now abandoned, and a continuation-in-part of application No. 09/450,810, filed on Nov. 29, 1999, now abandoned.

(51) Int. Cl.[7] .......................... C12Q 1/68; C07H 21/04; C07K 14/47

(52) U.S. Cl. ...................... 435/6; 536/23.5; 536/24.31; 530/350

(58) Field of Search ............................ 435/6; 536/23.5, 536/24.31; 530/350

(56) References Cited

U.S. PATENT DOCUMENTS 5,514,554 A    5/1996   Bacus ...................... 435/7.23

FOREIGN PATENT DOCUMENTS

| WO | 99/33869 | 7/1997 |
| WO | 98/18945 | 5/1998 |
| WO | 98/34118 | 8/1998 |
| WO | 99/23230 | 5/1999 |
| WO | 99/25877 | 5/1999 |
| WO | 00/08210 | 2/2000 |
| WO | WO-0137779 A2 * | 5/2001 |

OTHER PUBLICATIONS

Chang, G.T.G. et al. Characterization of a zinc–finger protein and its association with apoptosis in prostate cancer cells. Journal of the National Cancer Institute 92(17):1414–1421 (Sep. 2000).*

Momeni, P. et al. Mutations a new gene, encoding a zinc–finger protein, cause tricho–rhino–phalangeal syndrome type I. Nature Genetics 24:71–74 (Jan. 2000).*

Williams, et al., "Analysis of differential protein expression in normal and neoplastic human breast epithelial cell lines," *Electrophoresis* 19:333–343 (1998).

Yang, et al., "Combining SSH and cDNA microarrays for rapid identification of differentially expressed genes," *Nucleic Acids Research* 27(6):1517–1523 (1999).

DeRisi, et al., "Use of a cDNA microarray to analyse gene expression patterns in human cancer," *Nature Genetics* 14:457–460 (1996).

Welford, et al., "Detection of differentially expressed genes in primary tumor tissues using representational differences analysis coupled to microarray hybridizaiton" *Nucleic Acids Research* 26(12):3509–3065 (1998).

Khan, et al., "Expression profiling in cancer using cDNA microarrays," *Electrophoresis* 20:223–229 (1999).

Payne, et al., Primary Structure, Functional Expression, and Chromosomal Localization of the Bumetanide–sensitive Na–K–Cl Cotransporter in Human Colon, *J. Biol. Chem.* 270(30):17977–17985 (1995).

(List continued on next page.)

*Primary Examiner*—Carla J. Myers
*Assistant Examiner*—Diana Johannsen
(74) *Attorney, Agent, or Firm*—Albert P. Halluin; Viola T. Kung; Howrey, Simon, Arnold & White LLP

(57) ABSTRACT

Described herein are methods that can be used for diagnosis and prognosis of breast cancer. Also described herein are methods that can be used to screen candidate bioactive agents for the ability to modulate breast cancer. Additionally, methods and molecular targets (genes and their products) for therapeutic intervention in breast cancer are described.

8 Claims, 4 Drawing Sheets

OTHER PUBLICATIONS

King, et al., "Expression, purification and characterization of a mouse–human chimeric antibody and chimeric Fab' fragment," *Biochem. J.* 281:317–323 (1992).

Yamamoto et al., "Clinical application of chimeric monoclonal antibody A7–NCS conjugate," *Biotherapy*, 10(3):365–367 (1996) (Abstract).

Momeni et al., "Mutations in a new gene, encoding a zinc–finger protein, cause tricho–rhino–phalangeal syndrome type 1," *Nat Genet* 24:71–74 (Jan. 2000).

NCBI GenBank database printoutm Acc. No. AF183810, *Homo sapiens* zinc finger transcription factor TRPS1 mRNA. Momeni et al., *Nat Genet* 24:71–74 (Jan. 2000).

* cited by examiner

FIGURE 1A

```
TTCCTCCGCGAAGGCTCCTTTGATATTAATAGTGTTGGTGTCTTGAAACTGACGTAATGCGCGG
AGACTGAGGTCCTGACAAGCGATAACATTTCTGATAAAGACCCGATCTTACTGCAATCTCTAG
CGTCCTCTTTTTTGGTGCTGCTGGTTTCTCCAGACCTCGCGTCCTCTCGATTGCTCTCTCGCCTT
CCTATTTCTTTTTTTTTTTTTTAAACAAAAAACAACACCCCCTCCCCTCTCCCACCCGGCACCG
GGCACATCCTTGCTCTATTTCCTTTCTCTTTCTCTCTCTCTCTCTCTCTCTCTCTTTTTTAATAAG
GGTGGGGGAGGGAAAGGGGGGGGATGCAGGAAAGACCTTTTTCTCTCCCCCCCGCAATAATC
CAAGATCAACTCTGCAAACAACAGAAGACGGTTCATGGCTTTGGCCGCCGCGCCACCATCTTT
CGGGCTGCCGAGGGTGTTCTTGACGATTAATCAACAGATGTACAGATCAGCTCTCAAAATGTC
TTCTGTGTCTTCTGAGCGTCTTCTAAGACAATTGCATTAGCCTCCTGCTAGTTGACTAATAGAA
TTAATAATTGTAAAAAGCACTCTAAAGCCACATGCCTTATGAAGTCAATGCTGGGTATGATTT
TACAAAT[ATG]GTCCGGAAAAAGAACCCCCCTCTGAGAAACGTTGCAAGTGAAGGCGAGGGCC
AGATCCTGGAGCCTATAGGTACAGAAAGCAAGGTATCTGGAAAGAACAAAGAATTTTCTGCA
GATCAGATGTCAGAAAATACGGATCAGAGTGATGCTGCAGAACTAAATCATAAGGAGGAACA
TAGCTTGCATGTTCAAGATCCATCTTCTAGCAGTAAGAAGGACTTGAAAAGCGCAGTTCTGAG
TGAGAAGGCTGGCTTCAATTATGAAAGCCCCAGTAAGGGAGGAAACTTTCCCTCCTTTCCGCA
TGATGAGGTGACAGACAGAAATATGTTGGCTTTCTCATCTCCAGCTGCTGGGGGAGTCTGTGA
GCCCTTGAAGTCTCCGCAAAGAGCAGAGGCAGATGACCCTCAAGATATGGCCTGCACCCCTC
AGGGGACTCACTGGAGACAAAGGAAGATCAGAAGATGTCACCAAAGGCTACAGAGGAAACA
GGGCAAGCACAGAGTGGTCAAGCCAATTGTCAAGGTTTGAGCCCAGTTTCAGTGGCCTCAAA
AAACCCACAAGTGCCTTCAGATGGGGGTGTAAGACTGAATAAATCCAAAACTGACTTACTGG
TGAATGACAACCCAGACCCGGCACCTCTGTCTCCAGAGCTTCAGGACTTTAAATGCAATATCT
GTGGATATGGTTACTACGGCAACGACCCCACAGATCTGATTAAGCACTTCCGAAAGTATCACT
TAGGACTGCATAACCGCACCAGGCAAGATGCTGAGCTGGACAGCAAAATCTTGGCCCTTCAT
AACATGGTGCAGTTCAGCCATTCCAAAGACTTCCAGAAGGTCAACCGTTCTGTGTTTCTGGT
GTGCTGCAGGACATCAATTCTTCAAGGCCTGTTTTACTAAATGGGACCTATGATGTGCAGGTG
ACTTCAGGTGGAACATTCATTGGCATTGGACGGAAAACACCAGATTGCCAAGGGAACACCAA
GTATTTCCGCTGTAAATTCTGCAATTTCACTTATATGGGCAACTCATCCACCGAATTAGAACAA
CATTTTCTTCAGACTCACCCAAACAAAATAAAAGCTTCTCTCCCCTCCTCTGAGGTTGCAAAAC
CTTCAGAGAAAAACTCTAACAAGTCCATCCCTGCACTTCAATCCAGTGATTCTGGAGACTTGG
GAAAATGGCAGGACAAGATAACAGTCAAAGCAGGAGATGACACTCCTGTTGGGTACTCAGTG
CCCATAAAGCCCCTCGATTCCTCTAGACAAAATGGTACAGAGGCCACCAGTTACTACTGGTGT
AAATTTTGTAGTTTCAGCTGTGAGTCATCTAGCTCACTTAAACTGCTAGAACATTATGGCAAG
CAGCACGGAGCAGTGCAGTCAGGCGGCCTTAATCCAGAGTTAAATGATAAGCTTTCCAGGGG
CTCTGTCATTAATCAGAATGATCTAGCCAAAAGTTCAGAAGGAGAGACAATGACCAAGACAG
ACAAGAGCTCGAGTGGGGCTAAAAAGAAGGACTTCTCCAGCAAGGGAGCCGAGGATAATATG
GTAACGAGCTATAATTGTCAGTTCTGTGACTTCCGATATTCCAAAAGCCATGGCCCTGATGTA
ATTGTAGTGGGGCCACTTCTCCGTCATTATCAACAGCTCCATAACATTCACAAGTGTACCATTA
AACACTGTCCATTCTGTCCCAGAGGACTTTGCAGCCCAGAAAAGCACCTTGGAGAAATTACTT
ATCCGTTTGCTTGTAGAAAAAGTAATTGTTCCCACTGTGCACTCTTGCTTCTGCACTTGTCTCC
TGGGGCGGCTGGAAGCTCGCGAGTCAAACATCAGTGCCATCAGTGTTCATTCACCACCCCTGA
CGTAGATGTACTCCTCTTTCACTATGAAAGTGTGCATGAGTCCCAAGCATCGGATGTCAAACA
AGAAGCAAATCACCTGCAAGGATCGGATGGGCAGCAGTCTGTCAAGGAAAGCAAAGAACACT
CATGTACCAAATGTGATTTTATTACCCAAGTGGAAGAAGAGATTTCCCGACACTACAGGAGAG
CACACAGCTGCTACAAATGCCGTCAGTGCAGTTTTACAGCTGCCGATACTCAGTCACTACTGG
AGCACTTCAACACTGTTCACTGCCAGGAACAGGACATCACTACAGCCAACGGCGAAGAGGAC
GGTCATGCCATATCCACCATCAAAGAGGACCCCAAAATTGACTTCAGGGTCTACAATCTGCTA
ACTCCAGACTCTAAAATGGGAGAGCCAGTTTCTGAGAGTGTGGTGAAGAGAGAGAAGCTGGA
AGAGAAGGACGGGCTCAAAGAGAAAGTTTGGACCGAGAGTTCCAGTGATGACCTTCGCAATG
TGACTTGGAGAGGGGCAGACATCCTGCGGGGGAGTCCGTCATACACCCAAGCAAGCCTGGGG
CTGCTGACGCCTGTGTCTGGCACCCAAGAGCAGACAAAGACTCTAAGGGATAGTCCCAATGT
GGAGGCCGCCCATCTGGCGCGACCTATTTATGGCTTGGCTGTGGAAACCAAGGGATTCCTGCA
```

```
GGGGGCGCCAGCTGGCGGAGAGAAGTCTGGGGCCCTCCCCCAGCAGTATCCTGCATCGGGAG
AAAACAAGTCCAAGGATGAATCCCAGTCCCTGTTACGGAGGCGTAGAGGCTCCGGTGTTTTT
GTGCCAATTGCCTGACCACAAAGACCTCTCTCTGGCGAAAGAATGCAAATGGCGGATATGTAT
GCAACGCGTGTGGCCTCTACCAGAAGCTTCACTCGACTCCCAGGCCTTTAAACATCATTAAAC
AAAACAACGGTGAGCAGATTATTAGGAGGAGAACAAGAAAGCGCCTTAACCCAGAGGCACTT
CAGGCTGAGCAGCTCAACAAACAGCAGAGGGGCAGCAATGAGGAGCAAGTCAATGGAAGCC
CGTTAGAGAGGAGGTCAGAAGATCATCTAACTGAAAGTCACCAGAGAGAAATTCCACTCCCC
AGCCTAAGTAAATACGAAGCCCAGGGTTCATTGACTAAAAGCCATTCTGCTCAGCAGCCAGTC
CTGGTCAGCCAAACTTTGGATATTCACAAAAGGATGCAACCTTTGCACATTCAGATAAAAAGT
CCTCAGGAAAGTACTGGAGATCCAGGAAATAGTTCATCCGTATCTGAAGGGAAAGGAAGTTC
TGAGAGAGGCAGTCCTATAGAAAAGTACATGAGACCTGCGAAACACCCAAATTATTCACCAC
CAGGCAGCCCTATTGAAAAGTACCAGTACCCACTTTTTGGACTTCCCTTTGTACATAATGACTT
CCAGAGTGAAGCTGATTGGCTGCGGTTCTGGAGTAAATATAAGCTCTCCGTTCCTGGGAATCC
GCACTACTTGAGTCACGTGCCTGGCCTACCAAATCCTTGCCAAAACTATGTGCCTTATCCCACC
TTCAATCTGCCTCCTCATTTTTCAGCTGTTGGATCAGACAATGACATTCCTCTAGATTTGGCGA
TCAAGCATTCCAGACCTGGGCCAACTGCAAACGGTGCCTCCAAGGAGAAAACGAAGGCACCA
CCAAATGTAAAAAATGAAGGTCCCTTGAATGTAGTAAAAACAGAGAAAGTTGATAGAAGTAC
TCAAGATGAACTTTCAACAAAATGTGTGCACTGTGGCATTGTCTTTCTGGATGAAGTGATGTA
TGCTTTGCATATGAGTTGCCATGGTGACAGTGGACCTTTCCAGTGCAGCATATGCCAGCATCTT
TGCACGGACAAATATGACTTCACAACACATATCCAGAGGGGCCTGCATAGGAACAATGCACA
AGTGGAAAAAAATGGAAAACCTAAAGAG[TAA]AACCTTAGCACTTAGCACAATTAAATAGAA
ATAGGTTTTCTTGATGGGAATTCAATAGCTTGTAATGTCTTATGAAGACCTATTAAAAAAATA
CTTCATAGAGCCTGCCTTATCCAACATGAAATTCCCTTCTTTTGTTATTCTTTCTTTTGATGAGT
AGGTTACCAAGATTAAAAAGTGAGATAAATGGTCAATGAGAAAGAATGGAAGATGGTAAAC
AATCACTTTTTAAAACCTGTTAAGTCAAAACCATCTTGGCTAATATGTACTGGGGAAATAATC
CATAAGAGATATCACCAGACTAGAATTAATATATTTATAAAGAAAGAGACCAAAACTGTCTA
GAATTTGAAAGGGTTTACATATTATTATACTAAAGCAGTACTGGACTGGCCATTGGACCATTT
GTTCCAAAACCCATAAATTGTTGCCTAAATTTATAATGATCATGAAACCCTAGGCAGAGGAGG
AGAAATTGAAGGTCCAGGGCAATGAAAGAAAAATGGCGCCCTCTCAATTTAGTCTTCTCTCAT
TGGCCATGTTTCAGATTTTGACCTAGAAATGCGAGCTGTGGTTAGGCTTGGTTAGAGTGCAGC
AAGCAACATGACAGATGGTGGCACGCTGTTTTTACCCAGCCCTGCCTGTACATACACATGCAC
ACCCTCTCTGATATTTTTGTCCTTTAGATGTTCAAATACTCAGTAGTCCTTTTGTTTGCGGTTTA
GATTCATTTTGTCCACACATGTACCCATTTTAAAAAAACAATGTCCTCGATGCTTCTGTAGTGAT
TTCATTTTAGCCAGGTATTTCTTTCTTGTGTGTGATGAACCAGTATGGATTTGCTTTTCTAAGCC
TCCTGTTGGTTACTAATCTCACTTGGCACATTATAACTAAAGGAATCCCCTCAATTCAAAAGC
ATAGATGGATACAAATGTCAGACCGTGGGTTTAATTTGTTTAGAACACATGGCATTTCTTCAC
AAGGTAACCTGCTGTATTTATTTATTTTCTTTTGGTTAAATATAATTTCCAAACTTTGTGGTCAG
GCAGCGTCTAAGGTTACGTTACCACAGACTGACAGTTGGTATATGTACCAGCCAATCCCTTCA
TTAAATGTATACAGATTTAGTTAAGTAGCATTAAATAGGATTCTTAGAAGTATGTCCTCATAG
AACTTTTAATACTTAAGGCTTTGTAAAAACTATCCATGAAGGGAAAGCTCCTCAGCATAACTG
CTCAGGGAAATAGGGCTAAATAACTGAACATTAAATAATTGGTTAAAGGTGCTGTTAGTCGA
GCCTCAATGCTTGCTACAAGGATGTATGTACAAGGACTGACTTTAATAATTTGCATTATATTGT
CCCAACCAGTAGTTTATTTTTTGCCACGGAGATGTAGAAGATATTACAAGCTACTGGATGCAC
TGTCAGATTAACTTATTTCATTAAAGAAGTTGGGAGAACAAATAGGAAAAAAAAAACTTATTT
TTCTAGTAAATATTAATGTATTACATTTCAAATAATGGTGCCTGACATATTGAATAATTATTTT
CTACAGTGTACGTATGCAACAAAGATATTCCATCATGCATTAGAGTCAGTTCTGGCTCTGCCT
AGCTGTTTACATTTGCAAATGTAGCAAACAAGGTAATGAAGCAACTATTTCTATTGCAGTAGA
TATCCTTTTGTGTGTGTGTGTGTGCATTAAAGTTGTAAACGGTAACATGAAACAAATGAAAGT
TCTTGCTATAATGGTATGGAAAACAAGAAGGAAATGAAAATATTTTTATGCCTACTTAGGAAA
AAAAGGGTAGCACTTATTCATTCCAAGTACTTTTTTTTTTTAATTTTTAAGCTCTTAACTCACA
TTGTTATGCTTAAGATGATAAACATATATCCTCTTTTTATTGCTTTGTCTATGTTTCATATGAAA
CATTTCAGAAATTATTTTGATAAGTGTTGCTGGAATCTGCAACGCTGATTTTTTTTTGCATTCT
GTAGTCGCATTTGCACTCCATTTTTACATTAATTCGCAGTTGCTTTGTATCATTGTTTTGTTTGG
GTTTTGTTTCTTTTTCACAGTGCCGGGTCTTCGTTTCTTAAAGTTGGATGGCAGGTAGAGTTCA
ACCAGTTCGTGACTGTTGTAGCGAATGAAGTTAAAAAAATGTCTTTCTGATGTTGTGTTGTCAT
TTTCATTTTTGCATTTTTTTGTTTGCATATTAAAAAAAAGAGAAAAGAGAAAGCAAGAGACAGA
```

FIGURE 1B

```
AATCAGGACTAAGTCCTCTGCTTCAGTTTCATTGTTAACGGGCCTTATTCTGATCTCACCTGTC
GCGTAGCTCTAATATTCACATAAACTGAAATAAAGAAGTGGAATGAGGAGCTTTGACATTCA
AATTATGTGATGTAATTTATCTTCCTTAGGAATTTTGATGGATGCATCTCAAAATGTATAGCCA
GACTTGAGAGGTGACAATTAAAGATCTAAAAAAGAGAGGAGATTCCCCCAAACAACAATATT
TAATTTTCTTAGTAAAAAGAATAACAGAATGCATCGTGGCAATCCTTAAGCAACATTATCTAT
GTGGACTGCTTAAATCAGCAAAACACCAGAAGTTTGGTTAACTTGGGCAATATGACAAGTATT
ACTTTTTGGGCAAAACTACTCATTAAGCAATTTCTCTAGTGTGTCGGACACAAATAGGTTCTTT
ATTTTTGGCATGTATGCCTTTTATTTTCATTCAATTTTTTTTTTTCTCAGACAGACATAGTAG
TATCAACTAGCATTGGAAAATACATATCACTATTCTTGGAATATTTATGGTCAGTCTACTTTTT
AGTAAAATATTTTTGGATAGCGTTGACACGATAGATCTTATTCCATACTTCTTTATTATTGATA
ATTTTATTTTCATTTTTTGCTTTCATTATTATACATATTTGGTGGAGAAGAGGTTGGGCTTTTT
TGAAAGAGACAAAAATTTATTATAACACTAAACACTCCTTTTTTGACATATTAAAGCCTTTATT
CCATCTCTCAAGATATATTATAAAATTTATTTTTTTAATTTAAGATTTCTGAATTATTTTATCTT
AAATTGTGATTTTAAACGAGCTATTATGGTACGGAACTTTTTTTAATGAGGAATTTCATGATGA
TTTAGGAATTTTCTCTCTTGGAAAAGGCTTCCCCTGTGATGAAAATGATGTGCCAGCTAAAATT
GTGTGCCATTTAAAAACTGAAAATATTTTAAAATTATTTGTCTATATTCTAAATTGAGCTTTGG
ATCAAACTTTAGGCCAGGACCAGCTCATGCGTTCTCATTCTTCCTTTTCTCACTCTTTCTCTCAT
CACTCACCTCTGTATTCATTCTGTTGTTTGGGATAGAAAAATCATAAAGAGCCAACCCATCTC
AGAACGTTGTGGATTGAGAGAGACACTACATGACTCCAAGTATATGAGAAAAGGACAGAGCT
CTAATTGATAACTCTGTAGTTCAAAAGGAAAAGAGTATGCCCAATTCTCTCTACATGACATAT
TGAGATTTTTTTTAATCAACTTTTAAGATAGTGATGTTCTGTTCTAAACTGTTCTGTTTTAGTGA
AGGTAGATTTTTATAAAACAAGCATGGGGATTCTTTTCTAAGGTAATATTAATGAGAAGGGAA
AAAAGTATCTTTAACAGCTCTTTGTTGAAGCCTGTGGTAGCACATTATGTTTATAATTGCACAT
GTGCACATAATCTATTATGATCCAATGCAAATACAGCTCCAAAAATATTAAATGTATATATAT
TTTAAAATGCCTGAGGAAATACATTTTTCTTAATAAACTGAAGAGTCTCAGTATGGCTATTAA
AATAATTATTAGCCTCCTGTTGTGTGGCTGCAAAACATCACAAAGTGACCGGTCTTGAGACCT
GTGAACTGCTGCCCTGTTTAGTAAATAAAATTAATGCATTTCTAGAGGGGGAATATCTGCCAT
CCAGTGGTGGAAATGTGGAGTAAAGAAGCTGGTGGTCTGCTTCTGTGCTGTATGCCAGCCTTT
TGCCTTAAGTTGAGAGGAGGTCAACTTTAGCTACTGTCTTTGGTTTGAGAGCCATGGCAAAAA
AAAAAAAAGAAAAAAAGATCAAGTCGTCTTTGGTGAGCCAGTAAGGTGAAAGCTTGCTGACT
GTCCAAGGCACAAGAGAAAATTGAGGAATTGAAATGCAACCTGAGTATCAAACTAAATATTC
TAATCAAAGGTAGGTACTGTTAGGTGGAATTCTATCAGCAGGCAACTGCAAATGAGAAGAAG
ATAGAAGGACGCCCGTCGGGACTTTGGAGGGCATTGTTATTTTCCCAAAGAAAGACGGCCAA
GGGCAGAGGCATGGATTCTTTGCAGAGCACTTCCTTTTGGTTTTTCAGTACTGTTTCATAGACA
GTGGGCTCACATGTTCCTGATAGTGCTGCAGTTGCTTAGAAAGCATCCCAGTTAATTGCAGTA
ATTAGAACTTCTGGAATATGCTAGGGCAGAAGTATGTCAAGTATGTCACATGAAGAAAATGT
GAAATTCAAGAGTAATCCACACGTGAGAAACTAGACAATGTACATTCATGTGTTCTCTTGAAA
GGAAAGGGAGAGCTGTAAGCTTCACTCTGTCCTACACCGGAGAAAAGCAGGAATAACTTTAC
CGTGGAAATAATGTTTAGCTTTTATCAGAGAAAATTGTCCTTCTAGAGCATAGAGTCCCAAAA
CTCAATTCTGGTTTTCCCCTGTTTTTTTTTTTTTTTTTTTTTCCCAACATATGAACTGCAGCAT
ATCACTTTTTCTTTTTGTGCCTCAGGTTCCTCASCTGTAAAATTGAAAAATATATGTATTA
ATAATATTATTAATAATAATAATGGTAATGTAGTACTTGTTTGTAAAGCACTTTGAGATC
CTTGGTTGAAAGGCACCATAGGAGTGCCAAGTATTATTATGTGGCCAAGGGGGTTATTT
AAACTGTCAGTTCCCAAAGGCCAGGAAGGTTGGGGTCATTTTTCTTAAAGACGAGCTG
TAAATATCAACTAGGCAGCCAATAGTGTTGACTATGAAGATGCAAAACTATTACTAGGCT
GATAAAATCATAGTTTCTTAATGGCTACCAATAAGGCAAATATCACAATAATAAACGCCA
AATTCCTTAGGGCGGACTATTTGACAACCACATGGAAAACTTTGGGGGAGGCATGAGGG
GGGAACATCTCAAAATGCCAATGTAAAATTTAACTTACAGCAATATTCACCAGCAGAAAA
TGTCTTTCATATGGAATGATTTCATGTTGCTAAGAAAAAGAATTCAATTTGTAGTCCTGA
TTTGAATACTAGAATGTTGGCTATAATAGTTCTGTTCTTACAACACATGAAATTTTTTCGT
TTTATTTTATTTTGTTTTCATAGTGCATGTTCATTTCTACTCACAAACATGTTCTTGGTGT
ATTTCTTATGCAAACAATCTTCAGGCAGCAAAGATGTCTGTTACATCTAAACTTGAATAA
TAAAGTTTTACCACCAGTTACACATAACGGCGTTGGTATGGTTTATATGGATTCACTTTC
ATCCTTCTAGGCAATAGGGAAATACAGATCATTGTAATATATATATATATATATACAGGC
TCTGCTGAANTGAAATGGTGAAATCAAATCACCATTCTAAAAAATTATTACTTATATTGA
TAAAGCCTGGANTCTCTCAACTTGTTTTGCTTTGCTTTTTTTCTTTAACCAATCAATCTCT
TACTGATAGAGTTTGTGTAAAAAGATATATACTAGTTTCTTCAGAAAGATTAACAATAAA
AATTGTGTTTATTTCAAAAAAAAAAA
```

FIGURE 1C

MVRKKNPPLRNVASEGEGQILEPIGTESKVSGKNKEFSADQMSENTDQSDAAELNHKEEHSLHVQ
DPSSSSKKDLKSAVLSEKAGFNYESPSKGGNFPSFPHDEVTDRNMLAFSSPAAGGVCEPLKSPQRA
EADDPQDMACTPSGDSLETKEDQKMSPKATEETGQAQSGQANCQGLSPVSVASKNPQVPSDGGV
RLNKSKTDLLVNDNPDPAPLSPELQDFKCNICGYGYYGNDPTDLIKHFRKYHLGLHNRTRQDAEL
DSKILALHNMVQFSHSKDFQKVNRSVFSGVLQDINSSRPVLLNGTYDVQVTSGGTFIGIGRKTPDC
QGNTKYFRCKFCNFTYMGNSSTELEQHFLQTHPNKIKASLPSSEVAKPSEKNSNKSIPALQSSDSGD
LGKWQDKITVKAGDDTPVGYSVPIKPLDSSRQNGTEATSYYWCKFCSFSCESSSSLKLLEHYGKQ
HGAVQSGGLNPELNDKLSRGSVINQNDLAKSSEGETMTKTDKSSSGAKKKDFSSKGAEDNMVTS
YNCQFCDFRYSKSHGPDVIVVGPLLRHYQQLHNIHKCTIKHCPFCPRGLCSPEKHLGEITYPFACRK
SNCSHCALLLLHLSPGAAGSSRVKHQCHQCSFTTPDVDVLLFHYESVHESQASDVKQEANHLQGS
DGQQSVKESKEHSCTKCDFITQVEEEISRHYRRAHSCYKCRQCSFTAADTQSLLEHFNTVHCQEQD
ITTANGEEDGHAISTIKEEPKIDFRVYNLLTPDSKMGEPVSESVVKREKLEEKDGLKEKVWTESSSD
DLRNVTWRGADILRGSPSYTQASLGLLTPVSGTQEQTKTLRDSPNVEAAHLARPIYGLAVETKGFL
QGAPAGGEKSGALPQQYPASGENKSKDESQSLLRRRRGSGVFCANCLTTKTSLWRKNANGGYVC
NACGLYQKLHSTPRPLNIIKQNNGEQIIRRRTRKRLNPEALQAEQLNKQQRGSNEEQVNGSPLERR
SEDHLTESHQREIPLPSLSKYEAQGSLTKSHSAQQPVLVSQTLDIHKRMQPLHIQIKSPQESTGDPGN
SSSVSEGKGSSERGSPIEKYMRPAKHPNYSPPGSPIEKYQYPLFGLPFVHNDFQSEADWLRFWSKY
KLSVPGNPHYLSHVPGLPNPCQNYVPYPTFNLPPHFSAVGSDNDIPLDLAIKHSRPGPTANGASKEK
TKAPPNVKNEGPLNVVKTEKVDRSTQDELSTKCVHCGIVFLDEVMYALHMSCHGDSGPFQCSICQ
HLCTDKYDFTTHIQRGLHRNNAQVEKNGKPKE

FIGURE 2

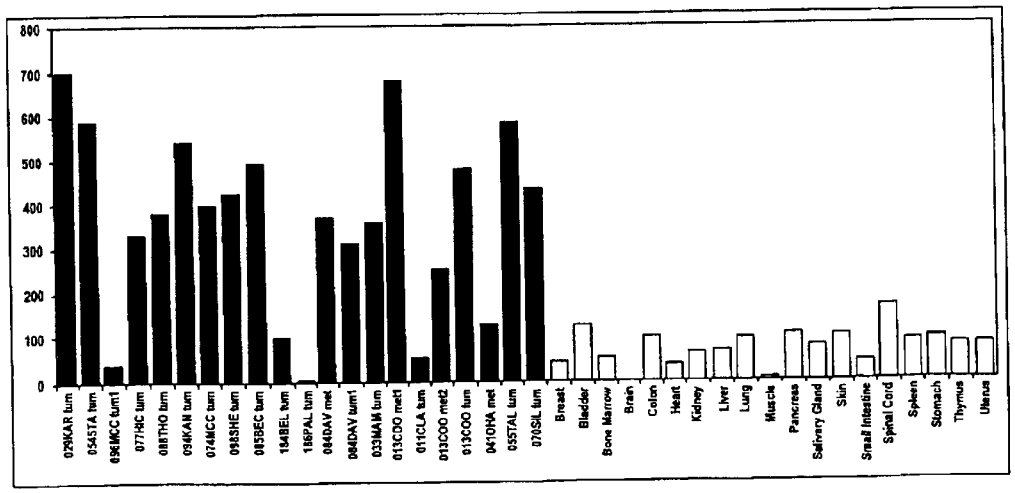

FIGURE 3

SEQUENCE LISTING

<160> NUMBER OF SEQ ID NOS: 3

<210> SEQ ID NO 1
<211> LENGTH: 10315
<212> TYPE: DNA
<213> ORGANISM: Homo sapiens
<220> FEATURE:
<221> NAME/KEY: misc_feature
<222> LOCATION: (10118)..(10180)
<223> OTHER INFORMATION: "n" at positions 10118 and 10180 can be any base.

<400> SEQUENCE: 1

| | | | | | |
|---|---|---|---|---|---|
| ttcctccgcg | aaggctcctt | tgatattaat | agtgttggtg | tcttgaaact | gacgtaatgc | 60 |
| gcggagactg | aggtcctgac | aagcgataac | atttctgata | agacccgat | cttactgcaa | 120 |
| tctctagcgt | cctctttttt | ggtgctgctg | gtttctccag | acctcgcgtc | ctctcgattg | 180 |
| ctctctcgcc | ttcctatttc | tttttttttt | ttttaaacaa | aaaacaacac | cccctcccct | 240 |
| ctcccacccg | gcaccgggca | catccttgct | ctatttcctt | tctctttctc | tctctctctc | 300 |
| tctcttttt | aataagggtg | ggggagggaa | aggggggga | ggcaggaaag | accttttct | 360 |
| ctcccccccg | caataatcca | agatcaactc | tgcaaacaac | agaagacggt | tcatggcttt | 420 |
| ggccgccgcg | ccaccatctt | tcgggctgcc | gagggtgttc | ttgacgatta | atcaacagat | 480 |
| gtacagatca | gctctcaaaa | tgtcttctgt | gtcttctgag | cgtcttctaa | gacaattgca | 540 |
| ttagcctcct | gctagttgac | taatagaatt | aataattgta | aaaagcactc | taaagccaca | 600 |
| tgccttatga | agtcaatgct | gggtatgatt | ttacaaatat | ggtccggaaa | aagaaccccc | 660 |
| ctctgagaaa | cgttgcaagt | gaaggcgagg | gccagatcct | ggagcctata | ggtacagaaa | 720 |
| gcaaggtatc | tggaaagaac | aaagaattct | ctgcagatca | gatgtcagaa | aatacggatc | 780 |
| agagtgatgc | tgcagaacta | aatcataagg | aggaacatag | cttgcatgtt | caagatccat | 840 |
| cttctagcag | taagaaggac | ttgaaaagcg | cagttctgag | tgagaaggct | ggcttcaatt | 900 |
| atgaaagccc | cagtaaggga | ggaaactttc | cctcctttcc | gcatgatgag | gtgacagaca | 960 |
| gaaatatgtt | ggctttctca | tttccagctg | ctgggggagt | ctgtgagccc | ttgaagtctc | 1020 |
| cgcaaagagc | agaggcagat | gaccctcaag | atatggcctg | caccccctca | ggggactcac | 1080 |
| tggagacaaa | ggaagatcag | aagatgtcac | caaaggctac | agaggaaaca | gggcaagcac | 1140 |
| agagtggtca | agccaattgt | caaggtttga | gcccagtttc | agtggcctca | aaaaacccac | 1200 |
| aagtgccttc | agatgggggt | gtaagactga | ataaatccaa | aactgactta | ctggtgaatg | 1260 |
| acaacccaga | cccggcacct | ctgtctccag | agcttcagga | cttttaaatgc | aatatctgtg | 1320 |
| gatatggtta | ctacggcaac | gaccccacag | atctgattaa | gcacttccga | aagtatcact | 1380 |
| taggactgca | taaccgcacc | aggcaagatg | ctgagctgga | cagcaaaatc | ttggcccttc | 1440 |
| ataacatggt | gcagttcagc | cattccaaag | acttccagaa | ggtcaaccgt | tctgtgtttt | 1500 |
| ctggtgtgct | gcaggacatc | aattcttcaa | ggcctgtttt | actaaatggg | acctatgatg | 1560 |
| tgcaggtgac | ttcaggtgga | acattcattg | gcattggacg | gaaaacacca | gattgccaag | 1620 |
| ggaacaccaa | gtatttccgc | tgtaaattct | gcaatttcac | ttatatgggc | aactcatcca | 1680 |
| ccgaattaga | acaacatttt | cttcagactc | acccaaacaa | aataaaagct | tctctcccct | 1740 |
| cctctgaggt | tgcaaaacct | tcagagaaaa | actctaacaa | gtccatccct | gcacttcaat | 1800 |
| ccagtgattc | tggagacttg | ggaaaatggc | aggacaagat | aacagtcaaa | gcaggagatg | 1860 |

-continued

```
acactcctgt tgggtactca gtgcccataa agcccctcga ttcctctaga caaaatggta    1920
cagaggccac cagttactac tggtgtaaat tttgtagttt cagctgtgag tcatctagct    1980
cacttaaact gctagaacat tatggcaagc agcacggagc agtgcagtca ggcggcctta    2040
atccagagtt aaatgataag ctttccaggg gctctgtcat taatcagaat gatctagcca    2100
aaagttcaga aggagagaca atgaccaaga cagacaagag ctcgagtggg gctaaaaaga    2160
aggacttctc cagcaaggga gccgaggata atatggtaac gagctataat tgtcagttct    2220
gtgacttccg atattccaaa agccatggcc ctgatgtaat tgtagtgggg ccacttctcc    2280
gtcattatca acagctccat aacattcaca agtgtaccat aaacactgt ccattctgtc     2340 ccagaggact ttgcagccca gaaaagcacc ttggagaaat tacttatccg tttgcttgta    2400
gaaaaagtaa ttgttcccac tgtgcactct tgcttctgca cttgtctcct ggggcggctg    2460
gaagctcgcg agtcaaacat cagtgccatc agtgttcatt caccacccct gacgtagatg    2520
tactcctctt tcactatgaa agtgtgcatg agtcccaagc atcggatgtc aaacaagaag    2580
caaatcacct gcaaggatcg gatgggcagc agtctgtcaa ggaaagcaaa gaacactcat    2640
gtaccaaatg tgattttatt acccaagtgg aagaagagat tccccgacac tacaggagag    2700
cacacagctg ctacaaatgc cgtcagtgca gttttacagc tgccgatact cagtcactac    2760
tggagcactt caaacactgtt cactgccagg aacaggacat cactacagcc aacgcgaag    2820 aggacggtca tgccatatcc accatcaaag aggagcccaa aattgacttc agggtctaca    2880
atctgctaac tccagactct aaaatggag agccagtttc tgagagtgtg gtgaagagag     2940
agaagctgga agagaaggac gggctcaaag agaaagtttg gaccgagagt tccagtgatg    3000
accttcgcaa tgtgacttgg agagggcag acatcctgcg ggggagtccg tcatacaccc    3060
aagcaagcct ggggctgctg acgcctgtgt ctggcaccca agagcagaca aagactctaa    3120
gggatagtcc caatgtggag gccgcccatc tggcgcgacc tatttatggc ttggctgtgg    3180
aaaccaaggg attcctgcag ggggcgccag ctggcggaga aagtctggg gccctccccc     3240 agcagtatcc tgcatcggga gaaaacaagt ccaaggatga atcccagtcc ctgttacgga    3300
ggcgtagagg ctccggtgtt ttttgtgcca attgcctgac cacaaagacc tctctctggc    3360
gaaagaatgc aaatggcgga tatgtatgca acgcgtgtgg cctctaccag aagcttcact    3420
cgactcccag gcctttaaac atcattaaac aaaacaacgg tgagcagatt attaggagga    3480
gaacaagaaa gcgccttaac ccagaggcac ttcaggctga gcagctcaac aaacagcaga    3540
ggggcagcaa tgaggagcaa gtcaatggaa gcccgttaga gaggaggtca gaagatcatc    3600
taactgaaag tcaccagaga gaaattccac tccccagcct aagtaaatac gaagcccagg    3660
gttcattgac taaaagccat tctgctcagc agccagtcct ggtcagccaa actctggata    3720
ttcacaaaag gatgcaacct ttgcacattc agataaaaag tcctcaggaa agtactggag    3780
atccaggaaa tagttcatcc gtatctgaag ggaaggaag ttctgagaga ggcagtccta     3840
tagaaaagta catgagacct gcgaaacacc caattattc accaccaggc agccctattg     3900
aaaagtacca gtacccactt tttggacttc cctttgtaca taatgacttc cagagtgaag    3960
ctgattggct gcggttctgg agtaaatata gctctccgt tcctgggaat ccgcactact     4020
tgagtcacgt gcctggccta ccaaatcctt gccaaaacta tgtgccttat ccacccttca    4080
atctgcctcc tcatttttca gctgttggat cagacaatga cattcctcta gatttggcga    4140
tcaagcattc cagacctggg ccaactgcaa acggtgcctc caaggagaaa acgaaggcac    4200
caccaaatgt aaaaaatgaa ggtcccttga atgtagtaaa aacagagaaa gttgatagaa    4260
```

-continued

```
gtactcaaga tgaactttca acaaaatgtg tgcactgtgg cattgtcttt ctggatgaag    4320
tgatgtatgc tttgcatatg agttgccatg gtgacagtgg acctttccag tgcagcatat    4380
gccagcatct ttgcacggac aaatatgact tcacaacaca tatccagagg ggcctgcata    4440
ggaacaatgc acaagtggaa aaaaatggaa acctaaaga gtaaaacctt agcacttagc    4500
acaattaaat agaaataggt tttcttgatg ggaattcaat agcttgtaat gtcttatgaa    4560
gacctattaa aaaatacttt catagagcct gccttatcca acatgaaatt cccttctttt    4620
gttattcttt cttttgatga gtaggttacc aagattaaaa agtgagataa atggtcaatg    4680
agaaagaatg gaagatggta acaatcact ttttaaaacc tgttaagtca aaaccatctt     4740
ggctaatatg tactggggaa ataatccata agagatatca ccagactaga attaatatat    4800
ttataaagaa agagaccaaa actgtctaga atttgaaagg gtttacatat tattatacta    4860
aagcagtact ggactggcca ttggaccatt tgttccaaaa cccataaatt gttgcctaaa    4920
tttataatga tcatgaaacc ctaggcagag gaggagaaat tgaaggtcca gggcaatgaa    4980
agaaaaatgg cgccctctca atttagtctt ctctcattgg ccatgtttca gattttgacc    5040
tagaaatgcg agctgtggtt aggcttggtt agagtgcagc aagcaacatg acagatggtg    5100
gcacgctgtt tttacccagc cctgcctgta catacacatg cacaccctct ctgatatttt    5160
tgtcctttag atgttcaaat actcagtagt ccttttgttt gcggtttaga ttcattttgt    5220
ccacacatgt acccatttta aaaacaatg tcctcgatgc ttctgtagtg atttcatttt     5280
agccaggtat ttctttcttg tgtgtgatga accagtatgg atttgctttt ctaagcctcc    5340
tgttggttac taatctcact tggcacatta taactaaagg aatcccctca attcaaaagc    5400
atagatggat acaaatgtca gaccgtgggt ttaatttgtt tagaacacat ggcatttctt    5460
cacaaggtaa cctgctgtat ttatttattt tcttttggtt aaatataatt tccaaacttt    5520
gtggtcaggc agcgtctaag gttacgttac cacagactga cagttggtat atgtaccagc    5580
caatcccttc attaaatgta tacagattta gttaagtagc attaaatagg attcttagaa    5640
gtatgtcctc atagaacttt taatacttaa ggctttgtaa aaactatcca tgaagggaaa    5700
gctcctcagc ataactgctc agggaaatag ggctaaataa ctgaacatta ataattggt     5760
taaaggtgct gttagtcgag cctcaatgct tgctacaagg atgtatgtac aaggactgac    5820
tttaataatt tgcattatat tgtcccaacc agtagtttat tttttgccac ggagatgtag    5880
aagatattac aagctactgg atgcactgtc agattaactt atttcattaa agaagttggg    5940
agaacaaata ggaaaaaaaa aacttatttt tctagtaaat attaatgtat tacatttcaa    6000
ataatggtgc ctgacatatt gaataattat tttctacagt gtacgtatgc aacaaagata    6060
ttccatcatg cattagagtc agttctggct ctgcctagct gtttacattt gcaaatgtag    6120
caaacaaggt aatgaagcaa ctatttctat tgcagtagat atccttttgt gtgtgtgtgt    6180
gtgcattaaa gttgtaaacg gtaacatgaa acaaatgaaa gttcttgcta taatggtatg    6240
gaaaacaaga aggaaatgaa aatattttta tgcctactta ggaaaaaaag ggtagcactt    6300
attcattcca agtactttt ttttttttaat ttttaagctc ttaactcaca ttgttatgct     6360
taagatgata aacatatatc ctctttttat tgctttgtct atgtttcata tgaaacattt    6420
cagaaattat tttgataagt gttgctggaa tctgcaacgc tgattttttt ttgcattctg    6480
tagtcgcatt tgcactccat ttttacatta attcgcagtt gctttgtatc attgttttgt    6540
ttgggttttg tttctttttc acagtgccgg gtcttcgttt cttaaagttg gatggcaggt    6600
```

| | |
|---|---|
| agagttcaac cagttcgtga ctgttgtagc gaatgaagtt aaaaaaatgt ctttctgatg | 6660 |
| ttgtgttgtc attttcattt ttgcatttt ttgtttgcat attaaaaaaa gagaaaagag | 6720 |
| aaagcaagag acagaaatca ggactaagtc ctctgcttca gtttcattgt taacgggcct | 6780 |
| tattctgatc tcacctgtcg cgtagctcta atattcacat aaactgaaat aaagaagtgg | 6840 |
| aatgaggagc tttgacattc aaattatgtg atgtaattta tcttccttag gaattttgat | 6900 |
| ggatgcatct caaatgtat agccagactt gagaggtgac aattaaagat ctaaaaaga | 6960 |
| gaggagattc ccccaaacaa caatatttaa ttttcttagt aaaagaata acagaatgca | 7020 |
| tcgtggcaat ccttaagcaa cattatctat gtggactgct taaatcagca aaacaccaga | 7080 |
| agtttggtta acttgggcaa tatgacaagt attacttttt gggcaaaact actcattaag | 7140 |
| caatttctct agtgtgtcgg acacaaatag gttcttatt tttggcatgt atgcctttt | 7200 |
| attttcattc aattttttt ttttctcaga cagacatagt agtatcaact agcattggaa | 7260 |
| aatacatatc actattcttg gaatatttat ggtcagtcta cttttagta aaatatttt | 7320 |
| ggatagcgtt gacacgatag atcttattcc atacttcttt attattgata attttatttt | 7380 |
| catttttgc tttcattatt atacatattt tggtggagaa gaggttgggc ttttttgaaa | 7440 |
| gagacaaaaa tttattataa cactaaacac tccttttttg acatattaaa gcctttattc | 7500 |
| catctctcaa gatatattat aaaatttatt tttttaattt aagatttctg aattatttta | 7560 |
| tcttaaattg tgattttaaa cgagctatta tggtacggaa cttttttaa tgaggaattt | 7620 |
| catgatgatt taggaatttt ctctcttgga aaaggcttcc cctgtgatga aaatgatgtg | 7680 |
| ccagctaaaa ttgtgtgcca tttaaaaact gaaaatattt taaaattatt tgtctatatt | 7740 |
| ctaaattgag ctttggatca aactttaggc caggaccagc tcatgcgttc tcattcttcc | 7800 |
| ttttctcact cttctctca tcactcacct ctgtattcat tctgttgttt gggatagaaa | 7860 |
| aatcataaag agccaaccca tctcagaacg ttgtggattg agagacac tacatgactc | 7920 |
| caagtatatg agaaaggac agagctctaa ttgataactc tgtagttcaa aaggaaaaga | 7980 |
| gtatgcccaa ttctctctac atgacatatt gagattttt ttaatcaact tttaagatag | 8040 |
| tgatgttctg ttctaaactg ttctgttta gtgaaggtag atttttataa aacaagcatg | 8100 |
| gggattcttt tctaaggtaa tattaatgag aagggaaaaa agtatcttta acagctcttt | 8160 |
| gttgaagcct gtggtagcac attatgttta taattgcaca tgtgcacata atctattatg | 8220 |
| atccaatgca aatacagctc caaaatatt aaatgtatat atattttaaa atgcctgagg | 8280 |
| aaatacattt ttcttaataa actgaagagt ctcagtatgg ctattaaaat aattattagc | 8340 |
| ctcctgttgt gtggctgcaa acatcacaa agtgaccggt cttgagacct gtgaactgct | 8400 |
| gccctgttta gtaaataaaa ttaatgcatt tctagagggg gaatatctgc catccagtgg | 8460 |
| tgaaatgtg gagtaaagaa gctggtggtc tgcttctgtg ctgtatgcca gccttttgcc | 8520 |
| ttaagttgag aggaggtcaa ctttagctac tgtctttggt ttgagagcca tggcaaaaaa | 8580 |
| aaaaaagaa aaaagatca agtcgtcttt ggtgagccag taaggtgaaa gcttgctgac | 8640 |
| tgtccaaggc acaagagaaa attgaggaat tgaaatgcaa cctgagtatc aaactaaata | 8700 |
| ttctaatcaa aggtaggtac tgttaggtgg aattctatca gcaggcaact gcaaatgaga | 8760 |
| agaagataga aggacgcccg tcgggacttt ggagggcatt gttatttcc caagaaaga | 8820 |
| cggccaaggg cagaggcatg gattcttgc agagcacttc cttttggttt ttcagtactg | 8880 |
| tttcatagac agtgggctca catgttcctg atagtgctgc agttgcttag aaagcatccc | 8940 |
| agttaattgc agtaattaga acttctggaa tatgctaggg cagaagtatg tcaagtatgt | 9000 |

-continued

```
cacatgaaga aaatgtgaaa ttcaagagta atccacacgt gagaaactag acaatgtaca    9060
ttcatgtgtt ctcttgaaag gaaagggaga gctgtaagct tcactctgtc ctacaccgga    9120
gaaaagcagg aataacttta ccgtggaaat aatgtttagc ttttatcaga gaaaattgtc    9180
cttctagagc atagagtccc aaaactcaat tctggttttc ccctgttttt tttttttttt    9240
tttttcccaa catatgaact gcagcatatc acttttctt tttgtgcctc aggttcctca     9300
cctgtaaaat tgaaaatat atgtattaat aatattatta ataataataa tggtaatgta     9360
gtacttgttt gtaaagcact ttgagatcct tggttgaaag gcaccatagg agtgccaagt    9420
attattatgt ggccaagggg gttatttaaa ctgtcagttc ccaaaggcca ggaaaggttg    9480
gggtcatttt tcttaaagac gagctgtaaa tatcaactag gcagccaata gtgttgacta    9540
tgaagatgca aaactattac taggctgata aaatcatagt ttcttaatgg ctaccaataa    9600
ggcaaatatc acaataataa acgccaaatt cctagggcg gactatttga caaccacatg     9660 gaaactttg ggggaggcat gagggggggaa catctcaaaa tgccaatgta aaatttaact    9720
tacagcaata ttcaccagca gaaaatgtct ttcatatgga atgatttcat gttgctaaga    9780
aaaagaattc aatttgtagt cctgatttga atactagaat gttggctata atagttctgt    9840
tcttacaaca catgaaattt tttcgtttta ttttattttg ttttcatagt gcatgttcat    9900
ttctactcac aaacatgttc ttggtgtatt tcttatgcaa acaatcttca ggcagcaaag    9960
atgtctgtta catctaaact tgaataataa agttttacca ccagttacac ataacggcgt    10020
tggtatggtt tatatggatt cactttcatc cttctaggca ataggaaat acagatcatt    10080 gtaatatata tatatatata tacaaggctc tgctgaantg aaatggtgaa atcaaatcac    10140
cattctaaaa aattattact tatattgata aagcctggan tctctcaact tgttttgctt    10200
tgcttttttt ctttaaccaa tcaatctctt actgatagat tttgtgtaaa aagatatata    10260
ctagtttctt cagaaagatt aacaataaaa attgtgttta tttcaaaaaa aaaaa         10315
```

<210> SEQ ID NO 2
<211> LENGTH: 1281
<212> TYPE: PRT
<213> ORGANISM: Homo sapiens

<400> SEQUENCE: 2

```
Met Val Arg Lys Lys Asn Pro Pro Leu Arg Asn Val Ala Ser Glu Gly
 1               5                  10                  15

Glu Gly Gln Ile Leu Glu Pro Ile Gly Thr Glu Ser Lys Val Ser Gly
             20                  25                  30

Lys Asn Lys Glu Phe Ser Ala Asp Gln Met Ser Glu Asn Thr Asp Gln
         35                  40                  45

Ser Asp Ala Ala Glu Leu Asn His Lys Glu Glu His Ser Leu His Val
     50                  55                  60

Gln Asp Pro Ser Ser Ser Lys Lys Asp Leu Lys Ser Ala Val Leu
 65                  70                  75              80

Ser Glu Lys Ala Gly Phe Asn Tyr Glu Ser Pro Ser Lys Gly Gly Asn
                 85                  90                  95

Phe Pro Ser Phe Pro His Asp Glu Val Thr Asp Arg Asn Met Leu Ala
            100                 105                 110

Phe Ser Phe Pro Ala Ala Gly Gly Val Cys Glu Pro Leu Lys Ser Pro
        115                 120                 125

Gln Arg Ala Glu Ala Asp Asp Pro Gln Asp Met Ala Cys Thr Pro Ser
    130                 135                 140
```

```
Gly Asp Ser Leu Glu Thr Lys Glu Asp Gln Lys Met Ser Pro Lys Ala
145                 150                 155                 160

Thr Glu Glu Thr Gly Gln Ala Gln Ser Gly Gln Ala Asn Cys Gln Gly
                165                 170                 175

Leu Ser Pro Val Ser Val Ala Ser Lys Asn Pro Gln Val Pro Ser Asp
                180                 185                 190

Gly Gly Val Arg Leu Asn Lys Ser Lys Thr Asp Leu Leu Val Asn Asp
                195                 200                 205

Asn Pro Asp Pro Ala Pro Leu Ser Pro Glu Leu Gln Asp Phe Lys Cys
210                 215                 220

Asn Ile Cys Gly Tyr Gly Tyr Gly Asn Asp Pro Thr Asp Leu Ile
225                 230                 235                 240

Lys His Phe Arg Lys Tyr His Leu Gly Leu His Asn Arg Thr Arg Gln
                245                 250                 255

Asp Ala Glu Leu Asp Ser Lys Ile Leu Ala Leu His Asn Met Val Gln
                260                 265                 270

Phe Ser His Ser Lys Asp Phe Gln Lys Val Asn Arg Ser Val Phe Ser
275                 280                 285

Gly Val Leu Gln Asp Ile Asn Ser Ser Arg Pro Val Leu Leu Asn Gly
290                 295                 300

Thr Tyr Asp Val Gln Val Thr Ser Gly Gly Thr Phe Ile Gly Ile Gly
305                 310                 315                 320

Arg Lys Thr Pro Asp Cys Gln Gly Asn Thr Lys Tyr Phe Arg Cys Lys
                325                 330                 335

Phe Cys Asn Phe Thr Tyr Met Gly Asn Ser Ser Thr Glu Leu Glu Gln
                340                 345                 350

His Phe Leu Gln Thr His Pro Asn Lys Ile Lys Ala Ser Leu Pro Ser
                355                 360                 365

Ser Glu Val Ala Lys Pro Ser Glu Lys Asn Ser Asn Lys Ser Ile Pro
370                 375                 380

Ala Leu Gln Ser Ser Asp Ser Gly Asp Leu Gly Lys Trp Gln Asp Lys
385                 390                 395                 400

Ile Thr Val Lys Ala Gly Asp Asp Thr Pro Val Gly Tyr Ser Val Pro
                405                 410                 415

Ile Lys Pro Leu Asp Ser Ser Arg Gln Asn Gly Thr Glu Ala Thr Ser
                420                 425                 430

Tyr Tyr Trp Cys Lys Phe Cys Ser Phe Ser Cys Glu Ser Ser Ser Ser
                435                 440                 445

Leu Lys Leu Leu Glu His Tyr Gly Lys Gln His Gly Ala Val Gln Ser
450                 455                 460

Gly Gly Leu Asn Pro Glu Leu Asn Asp Lys Leu Ser Arg Gly Ser Val
465                 470                 475                 480

Ile Asn Gln Asn Asp Leu Ala Lys Ser Ser Glu Gly Glu Thr Met Thr
                485                 490                 495

Lys Thr Asp Lys Ser Ser Ser Gly Ala Lys Lys Asp Phe Ser Ser
                500                 505                 510

Lys Gly Ala Glu Asp Asn Met Val Thr Ser Tyr Asn Cys Gln Phe Cys
                515                 520                 525

Asp Phe Arg Tyr Ser Lys Ser His Gly Pro Asp Val Ile Val Val Gly
530                 535                 540

Pro Leu Leu Arg His Tyr Gln Gln Leu His Asn Ile His Lys Cys Thr
545                 550                 555                 560
```

-continued

```
Ile Lys His Cys Pro Phe Cys Pro Arg Gly Leu Cys Ser Pro Glu Lys
                565                 570                 575

His Leu Gly Glu Ile Thr Tyr Pro Phe Ala Cys Arg Lys Ser Asn Cys
                580                 585                 590

Ser His Cys Ala Leu Leu Leu His Leu Ser Pro Gly Ala Ala Gly
                595                 600             605

Ser Ser Arg Val Lys His Gln Cys His Gln Cys Ser Phe Thr Thr Pro
610                 615                 620

Asp Val Asp Val Leu Leu Phe His Tyr Glu Ser Val His Glu Ser Gln
625                 630                 635                 640

Ala Ser Asp Val Lys Gln Glu Ala Asn His Leu Gln Gly Ser Asp Gly
                645                 650                 655

Gln Gln Ser Val Lys Glu Ser Lys Glu His Ser Cys Thr Lys Cys Asp
                660                 665                 670

Phe Ile Thr Gln Val Glu Glu Ile Ser Arg His Tyr Arg Arg Ala
            675                 680                 685

His Ser Cys Tyr Lys Cys Arg Gln Cys Ser Phe Thr Ala Ala Asp Thr
                690                 695                 700

Gln Ser Leu Leu Glu His Phe Asn Thr Val His Cys Gln Glu Gln Asp
705                 710                 715                 720

Ile Thr Thr Ala Asn Gly Glu Glu Asp Gly His Ala Ile Ser Thr Ile
                725                 730                 735

Lys Glu Glu Pro Lys Ile Asp Phe Arg Val Tyr Asn Leu Leu Thr Pro
                740                 745                 750

Asp Ser Lys Met Gly Glu Pro Val Ser Glu Ser Val Val Lys Arg Glu
                755                 760                 765

Lys Leu Glu Glu Lys Asp Gly Leu Lys Glu Lys Val Trp Thr Glu Ser
770                 775                 780

Ser Ser Asp Asp Leu Arg Asn Val Thr Trp Arg Gly Ala Asp Ile Leu
785                 790                 795                 800

Arg Gly Ser Pro Ser Tyr Thr Gln Ala Ser Leu Gly Leu Leu Thr Pro
                805                 810                 815

Val Ser Gly Thr Gln Glu Gln Thr Lys Thr Leu Arg Asp Ser Pro Asn
                820                 825                 830

Val Glu Ala Ala His Leu Ala Arg Pro Ile Tyr Gly Leu Ala Val Glu
                835                 840                 845

Thr Lys Gly Phe Leu Gln Gly Ala Pro Ala Gly Glu Lys Ser Gly
850                 855                 860

Ala Leu Pro Gln Gln Tyr Pro Ala Ser Gly Glu Asn Lys Ser Lys Asp
865                 870                 875                 880

Glu Ser Gln Ser Leu Leu Arg Arg Arg Gly Ser Gly Val Phe Cys
                885                 890                 895

Ala Asn Cys Leu Thr Thr Lys Thr Ser Leu Trp Arg Lys Asn Ala Asn
                900                 905                 910

Gly Gly Tyr Val Cys Asn Ala Cys Gly Leu Tyr Gln Lys Leu His Ser
                915                 920                 925

Thr Pro Arg Pro Leu Asn Ile Ile Lys Gln Asn Asn Gly Glu Gln Ile
                930                 935                 940

Ile Arg Arg Arg Thr Arg Lys Arg Leu Asn Pro Glu Ala Leu Gln Ala
945                 950                 955                 960

Glu Gln Leu Asn Lys Gln Gln Arg Gly Ser Asn Glu Glu Gln Val Asn
                965                 970                 975

Gly Ser Pro Leu Glu Arg Arg Ser Glu Asp His Leu Thr Glu Ser His
```

-continued

```
            980                   985                   990

Gln Arg Glu Ile Pro Leu Pro Ser Leu Ser Lys Tyr Glu Ala Gln Gly
        995                  1000                  1005

Ser Leu Thr Lys Ser His Ser Ala Gln Gln Pro Val Leu Val Ser Gln
   1010                  1015                  1020

Thr Leu Asp Ile His Lys Arg Met Gln Pro Leu His Ile Gln Ile Lys
1025                  1030                  1035                  1040

Ser Pro Gln Glu Ser Thr Gly Asp Pro Gly Asn Ser Ser Ser Val Ser
               1045                  1050                  1055

Glu Gly Lys Gly Ser Ser Glu Arg Gly Ser Pro Ile Glu Lys Tyr Met
           1060                  1065                  1070

Arg Pro Ala Lys His Pro Asn Tyr Ser Pro Pro Gly Ser Pro Ile Glu
       1075                  1080                  1085

Lys Tyr Gln Tyr Pro Leu Phe Gly Leu Pro Phe Val His Asn Asp Phe
   1090                  1095                  1100

Gln Ser Glu Ala Asp Trp Leu Arg Phe Trp Ser Lys Tyr Lys Leu Ser
1105                  1110                  1115                  1120

Val Pro Gly Asn Pro His Tyr Leu Ser His Val Pro Gly Leu Pro Asn
               1125                  1130                  1135

Pro Cys Gln Asn Tyr Val Pro Tyr Pro Thr Phe Asn Leu Pro Pro His
           1140                  1145                  1150

Phe Ser Ala Val Gly Ser Asp Asn Asp Ile Pro Leu Asp Leu Ala Ile
       1155                  1160                  1165

Lys His Ser Arg Pro Gly Pro Thr Ala Asn Gly Ala Ser Lys Glu Lys
   1170                  1175                  1180

Thr Lys Ala Pro Pro Asn Val Lys Asn Glu Gly Pro Leu Asn Val Val
1185                  1190                  1195                  1200

Lys Thr Glu Lys Val Asp Arg Ser Thr Gln Asp Glu Leu Ser Thr Lys
               1205                  1210                  1215

Cys Val His Cys Gly Ile Val Phe Leu Asp Glu Val Met Tyr Ala Leu
           1220                  1225                  1230

His Met Ser Cys His Gly Asp Ser Gly Pro Phe Gln Cys Ser Ile Cys
       1235                  1240                  1245

Gln His Leu Cys Thr Asp Lys Tyr Asp Phe Thr Thr His Ile Gln Arg
   1250                  1255                  1260

Gly Leu His Arg Asn Asn Ala Gln Val Glu Lys Asn Gly Lys Pro Lys
1265                  1270                  1275                  1280

Glu

<210> SEQ ID NO 3
<211> LENGTH: 5
<212> TYPE: PRT
<213> ORGANISM: Unknown Organism
<220> FEATURE:
<221> NAME/KEY: UNSURE
<222> LOCATION: (3)
<223> OTHER INFORMATION: “Xaa” at position 3 can be any base
<223> OTHER INFORMATION: Description of Unknown Organism:  cytokine
      receptor extracellular motif found in many species

<400> SEQUENCE: 3

Trp Ser Xaa Trp Ser
  1               5
```

METHODS OF DIAGNOSING BREAST CANCER

RELATED APPLICATIONS

This application is a continuation-in-part of U.S. Ser. No. 09/525,361 filed Mar. 15, 2000, a continuation-in-part of U.S. Ser. No. 09/453,137 filed Dec. 2, 1999, now abandoned, and a continuation-in-part of U.S. Ser. No. 09/450,810 filed Nov. 29, 1999, now abandoned.

FIELD OF THE INVENTION

The invention relates to the identification of expression profiles and the nucleic acids involved in breast cancer, and to the use of such expression profiles and nucleic acids in diagnosis and prognosis of breast cancer. The invention further relates to methods for identifying and using candidate agents and/or targets which modulate breast cancer.

BACKGROUND OF THE INVENTION

Breast cancer is a significant cancer in Western populations. It develops as the result of a pathologic transformation of normal breast epithelium to an invasive cancer. There have been a number of recently characterized genetic alterations that have been implicated in breast cancer. However, there is a need to identify all of the genetic alterations involved in the development of breast cancer.

Imaging of breast cancer for diagnosis has been problematic and limited. In addition, dissemination of tumor cells (metastases) to locoregional lymph nodes is an important prognostic factor; five year survival rates drop from 80 percent in patients with no lymph node metastases to 45 to 50 percent in those patients who do have lymph node metastases. A recent report showed that micrometastases can be detected from lymph nodes using reverse transcriptase-PCR methods based on the presence of mRNA for carcinoembryonic antigen, which has previously been shown to be present in the vast majority of breast cancers but not in normal tissues. Liefers et al., New England J. of Med. 339(4):223 (1998).

While academia and industry has made an effort to identify novel sequences, there has not been an equal effort exerted to identify the involvement of such sequences in disease states. For example, databases show the sequence for accession number AF183810, which encodes a polypeptide corresponding to a transcription factor, TRPS1. TRPS1 has been shown to contain multiple zinc-finger motifs and has been implicated in tricho-rhino-phalangeal syndrome type I, a malformation syndrome with craniofacial and skeletal abnormalities (Morneni, P. et al., Nat. Genet, 24:71–74 (2000)). However, no role in cancer has been ascribed to this protein until the present disclosure.

Thus, methods that can be used for diagnosis and prognosis of breast cancer would be desirable. Accordingly, provided herein are methods that can be used in diagnosis and prognosis of breast cancer. Further provided are methods that can be used to screen candidate bioactive agents for the ability to modulate breast cancer. Additionally, provided herein are molecular targets for therapeutic intervention in breast and other cancers.

SUMMARY OF THE INVENTION

The present invention provides methods for screening for compositions which modulate breast cancer.

In one aspect, a method of screening drug candidates comprises providing a cell that expresses an expression profile gene or fragments thereof. Preferred embodiments of the expression profile gene as described herein include the sequence comprising BFA4 or a fragment thereof. The method further includes adding a drug candidate to the cell and determining the effect of the drug candidate on the expression of the expression profile gene.

In one embodiment, the method of screening drug candidates includes comparing the level of expression in the absence of the drug candidate to the level of expression in the presence of the drug candidate, wherein the concentration of the drug candidate can vary when present, and wherein the comparison can occur after addition or removal of the drug candidate. In a preferred embodiment, the cell expresses at least two expression profile genes. The profile genes may show an increase or decrease.

Also provided herein is a method of screening for a bioactive agent capable of binding to a breast cancer modulating protein (BCMP) or a fragment thereof, the method comprising combining the BCMP or fragment thereof and a candidate bioactive agent, and determining the binding of the candidate agent to the BCMP or fragment thereof in a preferred embodiment, the BCMP is BFA4.

Further provided herein is a method for screening for a bioactive agent capable of modulating the bioactivity of a BCMP or a fragment thereof. In one embodiment, the method comprises combining the BCMP or fragment thereof and a candidate bioactive agent, and determining the effect of the candidate agent on the bioactivity of the BCMP or the fragment thereof. In a preferred embodiment the BCMP is BFA4.

Also provided herein is a method of evaluating the effect of a candidate breast cancer drug comprising administering the drug to a transgenic animal expressing or overexpressing a BCMP or a fragment thereof, or an animal lacking a BCMP for example as a result of a gene knockout in a preferred embodiment, the BCMP is BFA4.

Additionally, provided herein is a method of evaluating the effect of a candidate breast cancer drug comprising administering the drug to a patient and removing a cell sample from the patient The expression profile of the cell is then determined. This method may further comprise comparing the expression profile to an expression profile of a healthy individual.

Furthermore, a method of diagnosing breast cancer is provided. The method comprises determining the expression of a gene which encodes BFA4 or a fragment thereof in a first tissue type of a first individual, and comparing this to the expression of the gene from a second unaffected individual. A difference in the expression indicates that the first individual has breast cancer.

In another aspect, the present invention provides an antibody which specifically binds to BFA4, or a fragment thereof. Preferably the antibody is a monoclonal antibody. The antibody can be a fragment of an antibody such as a single stranded antibody as further described herein, or can be conjugated to another molecule. In one embodiment, the antibody is a humanized antibody.

In one embodiment a method for screening for a bioactive agent capable of interfering with the binding of BFA4 or a fragment thereof and an antibody which binds to said BFA4 or fragment thereof is provided. In a preferred embodiment, the method comprises combining BFA4 or a fragment thereof, a candidate bioactive agent and an antibody which binds to said BFA4 or fragment thereof. The method further includes determining the binding of said BFA4 or fragment thereof and said antibody Wherein there is a change in binding, an agent is identified as an interfering agent The interfering agent can be an agonist or an antagonist. Preferably, the antibody as well, as the agent inhibits breast cancer.

In one aspect of the invention, a method for inhibiting the activity of a breast cancer modulating protein are provided. The method comprises binding an inhibitor to the protein. In a preferred embodiment, the protein is BFA4.

In another aspect, the invention provides a method for neutralizing the effect of a breast cancer modulating protein. The method comprises contacting an agent specific for the protein with the protein in an amount sufficient to effect neutralization. In a preferred embodiment, the protein is BFA4.

In a further aspect, a method for treating or inhibiting breast cancer is provided. In one embodiment, the method comprises administering to a call a composition comprising an antibody to BFA4 or a fragment thereof. In one embodiment, the antibody is conjugated to a therapeutic moiety. Such therapeutic moieties include a cytotoxic agent and a radioisotope. The method can be performed in vitro or in vivo, preferably in vivo to an individual. In a preferred embodiment the method of inhibiting breast cancer is provided to an individual with such cancer.

As described herein, methods of treating or inhibiting breast cancer can be performed by administering an inhibitor of BFA4 activity to a cell or individual. In one embodiment a BFA4 inhibitor is an antisense molecule to a nucleic acid encoding BFA4.

Moreover, provided herein is a biochip comprising a nucleic acid segment which encodes BFA4, or a fragment thereof, wherein the biochip comprises fewer than 1000 nucleic acid probes. Preferably at least two nucleic acid segments are included.

Also provided herein are methods of eliciting an immune response in an individual. In one embodiment a method provided herein comprises administering to an individual a composition comprising BFA4 or a fragment thereof. In another aspect, said composition comprises a nucleic acid comprising a sequence encoding BFA4 or a fragment thereof.

Further provided herein are compositions capable of eliciting an immune response in an individual. In one embodiment a composition provided herein comprises BFA4 or a fragment thereof and a pharmaceutically acceptable carrier. In another embodiment, said composition comprises a nucleic acid comprising a sequence encoding BFA4 or a fragment thereof and a pharmaceutically acceptable carrier.

Other aspects of the invention will become apparent to the skilled artisan by the following description of the invention.

DETAILED DESCRIPTION OF THE FIGURES

FIGS. 1A–1C (SEQ ID NO:1) show an embodiment of a nucleic acid (mRNA) which includes a sequence which encodes a breast cancer protein provided herein, BFA4. The start and stop codons are shaded, designating an open reading frame. The underlined sequence corresponds to that of accession no. AA428090.

FIG. 2 (SEQ ID NO:2) shows an embodiment of an amino acid sequence of BFA4.

FIG. 3 shows an expression profiles with the relative amount of expression of BFA4 in various samples of breast cancer tissue (dark bars) and normal tissue types (light bars).

DETAILED DESCRIPTION OF THE INVENTION

The present invention provides novel methods for diagnosis and prognosis evaluation for breast cancer, as well as methods for screening for compositions which modulate breast cancer and compositions which bind to modulators of breast cancer. In one aspect, the expression levels of genes are determined in different patient samples for which either diagnosis or prognosis information is desired, to provide expression profiles. An expression profile of a particular sample is essentially a "fingerprint" of the state of the sample; while two states may have any particular gene similarly expressed, the evaluation of a number of genes simultaneously allows the generation of a gene expression profile that is unique to the state of the cell. That is, normal tissue may be distinguished from breast cancer tissue, and within breast cancer tissue, different prognosis states (good or poor long term survival prospects, for example) may be determined. By comparing expression profiles of breast cancer tissue in different states, information regarding which genes are important (including both up- and down-regulation of genes) in each of these states is obtained. The identification of sequences that are differentially expressed in breast cancer tissue versus normal breast tissue, as well as differential expression resulting in different prognostic outcomes, allows the use of this information in a number of ways. For example, the evaluation of a particular treatment regime may be evaluated: does a chemotherapeutic drug act to improve the long-term prognosis in a particular patient Similarly, diagnosis may be done or confirmed by comparing patient samples with the known expression profiles. Furthermore, these gene expression profiles (or individual genes) allow screening of drug candidates with an eye to mimicking or altering a particular expression profile; for example, screening can be done for drugs that suppress the breast cancer expression profile or convert a poor prognosis profile to a better prognosis profile. This may be done by making biochips comprising sets of the important breast cancer genes, which can then be used in these screens. These methods can also be done on the protein basis; that is, protein expression levels of the breast cancer proteins can be evaluated for diagnostic and prognostic purposes or to screen candidate agents. In addition, the breast cancer nucleic acid sequences can be administered for gene therapy purposes, including the administration of antisense nucleic acids, or the breast cancer proteins (including antibodies and other modulators thereon administered as therapeutic drugs.

Thus the present invention provides nucleic acid and protein sequences that are differentially expressed in breast cancer when compared to normal tissue. The differentially expressed sequences provided herein are termed "breast cancer sequences". As, outlined below, breast cancer sequences include those that are up-regulated (i.e. expressed at a higher level) in breast cancer, as well as those that are down-regulated (i.e. expressed at a lower level) in breast cancer. In a preferred embodiment, the breast cancer sequences are from humans; however, as will be appreciated by those in the art, breast cancer sequences from other organisms may be useful in animal models of disease and drug evaluation; thus, other breast cancer sequences are provided, from vertebrates, including mammals, including rodents (rats, mice, hamsters, guinea pigs, etc.), primates, farm animals (including sheep, goats, pigs, cows, horses, etc.). Breast cancer sequences from other organisms may be obtained using the techniques outlined below.

In a preferred embodiment, the breast cancer sequences are those of nucleic acids encoding BFA4 or fragments thereof. Preferably, the breast cancer sequence is that depicted in FIGS. 1A–1C (SEQ ID NO:1), or a fragment thereof. Preferably, the breast cancer sequences encode a protein having the amino acid sequence depicted in FIG. 2

(SEQ ID NO:2), or a fragment thereof. In a preferred embodiment, the breast cancer sequences encode human zinc finger transcription factor TRPS1.

Breast cancer sequences can include both nucleic acid and amino acid sequences. In a preferred embodiment, the breast cancer sequences are recombinant nucleic acids. By the term "recombinant nucleic acid" herein is meant nucleic acid, originally formed in vitro, in general, by the manipulation of nucleic acid by polymerases and endonucleases, in a form not normally found in nature. Thus an isolated nucleic acid. In a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and, compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a breast cancer protein from one organism in a different organism or host cell. Alternatively, the protein may be made at a significantly higher concentration than is normally seen, through the use of an inducible promoter or high expression promoter, such that the protein is made at increased concentration levels. Alternatively, the protein may be in a form not normally found in nature, as in the addition of an epitope tag or amino acid substitutions, insertions and deletions, as discussed below.

In a preferred embodiment, the breast cancer sequences are nucleic acids. As will be appreciated by those in the art and is more fully outlined below, breast cancer sequences are useful in a variety of applications, including diagnostic applications, which will detect naturally occurring nucleic acids, as well as screening applications; for example, biochips comprising nucleic acid probes to the breast cancer sequences can be generated. In the broadest sense, then, by "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramidate (Beau e et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include the with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Sac. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,508, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within one definition of nucleic acids (see Jenkins et al., Chem. Soc. Rev. (1995) pp169–176). Several nucleic acid analogs are described in Rawls, C & E News Jun. 2, 1997 page 35. All of these references are hereby expressly incorporated by reference. These modifications of the ribose-phosphate backbone may be done for a variety of reasons, for example to increase the stability and half-life of such molecules in physiological environments or as probes on a biochip.

As will be appreciated by those in the art all of these nucleic acid analogs may find use in the present invention. In addition, mixtures of naturally occurring nucleic acids and analogs can be made; alternatively, mixtures of different nucleic acid analogs, and mixtures of naturally occurring nucleic acids and analogs may be made.

Particularly preferred are peptide nucleic acids (PNA) which includes paptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature (Tm) for mismatched versus perfectly matched basepairs. DNA and RNA typically exhibit a 2–4° C. drop in Tm for an internal mismatch. With the non-ionic PNA backbone, the drop is closer to 7–9° C. Similarly, due to their non-ionic nature, hybridization of the bases attached to these backbones is relatively insensitive to salt concentration. In addition, PNAs are not degraded by cellular enzymes, and thus can be more stable.

The nucleic acids may be single stranded or double stranded, as specified, or contain portions of both double stranded or single stranded sequence. As will be appreciated by those in the art, the depiction of a single strand ("Watson") also defines the sequence of the other strand ("Crick"); thus the sequences described herein also includes the complement of the sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthine hypoxanthine, isocytosine, isoguanine, etc. As used herein, the term "nucleoside" includes nucleotides and nucleoside and nucleaotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

A breast cancer sequence can be initially identified by substantial nucleic acid and/or amino acid sequence homology to the breast cancer sequences outlined herein. Such homology can be based upon the overall nucleic acid or amino acid sequence, and is generally determined as outlined below, using either homology programs or hybridization conditions.

The breast cancer sequences of the invention can be identfied as follows. Samples of normal and tumor tissue are applied to biochips comprising nucleic acid probes. The samples are first microdissected, if applicable, and treated as is know in the art for the preparation of mRNA. Suitable biochips are commercially available, for example from Affymetrix. Gene expression profiles as described herein are generated, and the data analyzed.

The isolation of mRNA comprises isolating total cellular RNA by disrupting a cell and performing differential centrifugation. Once the total RNA is isolated, mRNA is isolated by making use of the adenine nucleotide residues known to those skilled in the art as a poly (A) tail found on virtually every eukaryotic mRNA molecule at the 3' end thereof. Oligonucleotides composed of only deoxythymidine [olgo(dT)] are linked to cellulose and the oligo(dT)-cellulose packed into small columns. When a preparation of total cellular RNA is passed through such a column, the mRNA molecules bind to the oligo(dT) by the poly (A) tails while the rest of the RNA flows through the column. The bound mRNAs are then eluted from the column and collected.

In a preferred embodiment, the genes showing changes in expression as between normal and disease states are compared to genes expressed in other normal tissues, including, but not limited to lung, heart, brain, liver, breast, kidney, muscle, prostate, small intestine, large intestine, spleen, bone, and placenta. In a preferred embodiment, those genes identified during the breast cancer screen that are expressed in any significant amount in other tissues are removed from the profile, although in some embodiments, this is not necessary. That is, when screening for drugs, it is preferable that the target be disease specific, to minimize possible side effects.

In a preferred embodiment, breast cancer sequences are those that are unregulated in breast cancer; that is, the expression of these genes is higher in breast carcinoma as compared to normal breast tissue. "Up-regulation" as used herein means at least about a 50% increase, preferably a two-fold change, more preferably at least about a three fold change, with at least about five-fold or higher being preferred. All accession numbers herein are for the GenBank sequence database and the sequences of the accession numbers are hereby expressly incorporated by reference. GenBank is known in the art, see, e.g., Benson, D A, et al., Nucleic Acids Research 26:1–7 (1998). In addition, these genes were found to be expressed in a limited amount or not at all in bladder, bone marrow, brain, colon, heart, kidney, liver, lung, muscle, pancreas, salivary gland, skin, small intestine, spinal cord, spleen, stomach, thymus and uterus.

In a preferred embodiment, BFA4 is up-regulated in breast cancer.

In another embodiment, breast cancer sequences are those that are down-regulated in breast cancer, that is, the expression of these genes is lower in, for example, breast carcinoma as compared to normal breast tissue. "Down-regulation" as used herein means at least about a two-fold change, preferably at least about a three fold change, with at least about five-fold or higher being preferred.

Breast cancer proteins of the present invention may be classified as secreted proteins, transmembrane proteins or intracellular proteins. In a preferred embodiment the breast cancer protein is an intracellular protein. Intracellular proteins may be found in the cytoplasm and/or in the nucleus. Intracellular proteins are involved in all aspects of cellular function and replication (including, for example, signaling pathways); aberrant expression of such proteins results in unregulated or disregulated cellular processes. For example, many intracellular proteins have enzymatic activity such as protein kinase activity, protein phosphatase activity, protease activity, nucleotide cyclase activity, polymerase activity and the like. Intracellular proteins also serve as docking proteins that are involved in organizing complexes of proteins, or targeting proteins to various subcellular localizations, and are involved in maintaining the structural integrity of organelles.

In a preferred embodiment, BFA4 is an intracellular protein, preferably found in the nucleus.

An increasingly appreciated concept in characterizing intracellular proteins is the presence in the proteins of one or more motifs for which defined functions have been attributed. In addition to the highly conserved sequences found in the enzymatic domain of proteins, highly conserved sequences have been identified in proteins that are involved in protein-protein interaction. For example, Src-homology-2 (SH2) domains bind tyrosine-phosphorylated targets in a sequence dependent manner. PTB domains, which are distinct from SH2 domains, also bind tyrosine phosphorylated targets. SH3 domains bind to proline-rich targets. In addition, PH domains, tetratricopepide repeats and WD domains to name only a few, have been shown to mediate protein-protein interactions. Some of these may also be involved in binding to phospholipids or other second messengers. As will be appreciated by one of ordinary skill in the art, these motifs can be identified on the basis of primary sequence; thus, an analysis of the sequence of proteins may provide insight into both the enzymatic potential of the molecule and/or molecules with which the protein may associate.

In a preferred embodiment, the breast cancer sequences are transmembrane proteins. Transmembrane proteins are molecules that span the phospholipid bilayer of a cell. They may have an intracellular domain, an extracellular domain, or both. The intracellular domains of such proteins may have a number of functions including those already described for intracellular proteins. For example, the intracellular domain may have enzymatic activity and/or may serve as a binding site for additional proteins. Frequently the intracellular domain of transmembrane proteins serves both roles. For example certain receptor tyrosine kinases have both protein kinase activity and SH2 domains. In addition, autophosphorylation of tyrosines on the receptor molecule itself, creates binding sites for additional SH2 domain containing proteins.

Transmembrane proteins may contain from one to many transmembrane domains. For example, receptor tyrosine kinases, certain cytokne receptors, receptor guanytyl cyciases and receptor serine/threonine protein kinases contain a single transmembrane domain. However, various other proteins including channels and adenytyl cyclases contain numerous transmembrane domains. Many important cell surface receptors are classified as "seven transmembrane domain" proteins, as they contain 7 membrane spanning regions. Important transmembrane protein receptors include, but are not limited to insulin receptor, insulin-like growth factor receptor, human growth hormone receptor, glucose transporters, transferrin receptor, epidermal growth factor receptor, low density lipoprotein receptor, epidermal growth factor receptor, leptin receptor, interleukin receptors, e.g. IL-1 receptor, IL-2 receptor, etc.

Characteristics of transmembrane domains include approximately 20 consecutive, hydrophobic amino acids that may be followed by charged amino acids. Therefore, upon analysis of the amino acid sequence of a particular protein, the localization and number of transmembrane domains within the protein may be predicted.

The extracellular domains of transmembrane proteins are diverse; however, conserved motifs are found repeatedly among various extracellular domains. Conserved structure and/or functions have been ascribed to different extracellular motifs. For example, cytokine receptors are characterized by a cluster of cysteines and a WSXWS (W=tryptophan, S=serine, X=any amino acid) motif (SEQ ID NO:3). Immunoglobulin-like domains are highly conserved. Mucin-like domains may be involved in cell adhesion and leucine-rich repeats participate in protein-protein interactions.

Many extracellular domains are involved in binding to other molecules. In one aspect, extracellular domains are receptors. Factors that bind the receptor domain include circulating ligands, which may be peptides, proteins, or small molecules such as adenosine and the like. For example, growth factors such as EGF, FGF and PDGF are circulating growth factors that bind to their cognate receptors to initiate a variety of cellular responses. Other factors include cytokines, mitogenic factors, neurotrophic factors and the like. Extracellular domains also bind to cell-associated molecules. In this respect, they mediate cell-cell interactions. Cell-associated ligands can be tethered to the cell for example via a glycosylphosphatidylinositol (GPI) anchor, or may themselves be transmembrane proteins. Extracellular domains also associate with the extracellular matrix and contribute to the maintenance of the cell structure.

Breast cancer proteins that are transmembrane are particularly preferred in the present invention as they are good targets for immunotherepeutics, as are described herein. In addition, as outlined below, transmembrane proteins can be also useful in imaging modalities.

It will also be appreciated by those in the art that a transmembrane protein can be made soluble by removing transmembrane sequences, for example through recombinant methods. Furthermore, transmembrane proteins that have been made soluble can be made to be secreted through recombinant means by adding an appropriate signal sequence In a preferred embodiment, the breast cancer proteins are separated proteins; the secretion of which can be either constitutive or regulated. These proteins have a signal peptide or signal sequence that targets the molecule to the secretory pathway. Secreted proteins are involved in numerous physiological events; by virtue of their circulating nature, they serve to transmit signals to various other cell types. The secreted protein may function in an autocrine manner (acting on the cell that secreted the factor), a paracrine manner (acting on cells in dose proximity to the cell that secreted the factor) or an endocrine manner (acting on cells at a distance). Thus secreted molecules find use in modulating or altering numerous aspects of physiology. Breast cancer proteins that are secreted proteins are particularly preferred in the present invention as they serve as good targets for diagnostic markers, for example for blood tests.

A breast cancer sequence is initially identified by substantial nucleic acid and/or amino acid sequence homology to the breast cancer sequences outlined herein. Such homology can be based upon the overall nucleic acid or amino acid sequence, and is generally determined as outlined below, using either homology programs or hybridization conditions.

As used herein, a nucleic acid is a "breast cancer nucleic acid" if the overall homology of the nucleic acid sequence to the nucleic acid sequences encoding the amino acid sequences of the figures is preferably greater than about 75%, more preferably greater than about 80%, even more preferably greater than about 85% and most preferably greater than 90%. In some embodiments the homology will be as high as about 93 to 95 or 98%. Homology in This context means sequence similarity or identity, with identity being preferred. A preferred comparison for homology purposes is to compare the sequence containing sequencing errors to the correct sequence. This homology will be determined using standard techniques known in the art, including, but not limited to, the local homology algorithm of Smith & Waterman, Adv. Appl. Math. 2:482 (1981), by the homology alignment algorithm of Needleman & Wunsch, J. Mol. Biool. 48:443 (1970), by the search for similarity method of Pearson & Lipman, PNAS USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res. 12:387–395 (1984), preferably using the default settings, or by inspection.

In a preferred embodiment, the sequences which are used to determine sequence identity or similarity are selected from the sequences set forth in the figures, preferably that shown in FIGS. 1A–1C (SEQ ID NO:1) and fragments thereof. In one embodiment the sequences utilized herein are those set forth in the figures. In another embodiment the sequences are naturally occurring allelic variants of the sequences set forth in the figures. In another embodiment the sequences are sequence variants as further described herein.

One example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351–360 (1987); the method is similar to that described by Higgins & Sharp CABIOS 5:151–153(1989). Useful PILEUP parameters including a default gap weight of 3.00, a default gap length weight of 0.10, and weighted end gaps.

Another example of a useful algorithm is the BLAST algorithm, described in Altschul et al., J. Mol. Biol. 215, 403–410, (1990) and Karlin et al., PNAS USA 90:5873–5787 (1993). A particularly useful BLAST program is the WU-BLAST-2 program which was obtained from Altschul et al., Methods in Enzymology, 266:460–480 (1996). WU-BLAST-2 uses several search parameters, most of which are set to the default values. The adjustable parameters are set with the following values: overlap span= 1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

Thus, "percent (%) nucleic acid sequence identity" is defined as the percentage of nucleotide residues in a candidate sequence that are identical with the nucleotide residues of FIGS. 1A–1C (SEQ ID NO:1). A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer nucleosides than those of the figures, it is understood that the percentage of homology will be determined based on the number of homologous nucleosides in relation to the total number of nucleosides. Thus, for example, homology of sequences shorter than those of the sequences identified herein and as discussed below, will be determined using the number of nucleosides in the shorter sequence.

In one embodiment, the nucleic acid homology is determined through hybridization studies. Thus, for example, nucleic acids which hybridize under high stringency to the nucleic acid sequences which encode the peptides identified in the figures, or their complements, are considered a breast cancer sequence. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5–10° C. lower than the thermal melting point (Tm) for the specific sequence at a defined ionic strength pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions Will be those in which the salt concentration is less than about 1.0M sodium ion, typically about 0.01 to 1.0M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

In another embodiment, less stringent hybridlzation conditions are used; for example, moderate or low stringency conditions may be used, as are known In the art; see Maniatis and Ausubel, supra, and Tijssen, supra.

In addition, the breast cancer nucleic acid sequences of the invention are fragments of larger genes, i.e. they are nucleic acid segments. "Genes" in this context includes coding regions, non-coding regions, and mixtures of coding and non-coding regions. Accordingly, as will be appreciated by those in the art, using the sequences provided herein, additional sequences of the breast cancer genes can be obtained, using techniques well known in the art for cloning either longer sequences or the full length sequences; see Maniatis et al., and Ausubel, et al., supra, hereby expressly incorporated by reference.

Once the breast cancer nucleic acid is identified, it can be cloned and, if necessary, its constituent parts recombined to form the entire breast cancer nucleic acid. Once isolated from its natural source, e.g., contained within a plasmid or other vector or excised therefrom as a linear nucleic acid segment, the recombinant breast cancer nucleic acid can be further-used as a probe to identify and isolate other "precursor" nucleic acid to make modified or variant breast cancer nucleic acids and proteins.

The breast cancer nucleic acids of the present invention are used in several ways. In a first embodiment, nucleic acid probes to the breast cancer nucleic acids are made and attached to biochips to be used in screening and diagnostic methods, as outlined below, or for administration, for example for gene therapy and/or antisense applications. Alternatively, the breast cancer nucleic acids that include coding regions of breast cancer proteins can be put into expression vectors for the expression of breast cancer proteins, again either for screening purposes or for administration to a patient.

In a preferred embodiment, nucleic acid probes to breast cancer nucleic acids (both the nucleic acid sequences encoding peptides outlined in the figures and/or the complements thereof) are made. The nucleic acid probes attached to the blochip are designed to be substantially complementary to the breast cancer nucleic acids, i.e. the target sequence (either the target sequence of the sample or to other probe sequences, for example in sandwich assays), such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions, particularly high stringency conditions, as outlined herein.

A nucleic acid probe is generally single stranded but can be partially single and partially double stranded. The strandedness of the probe is dictated by the structure, composition, and properties of the target sequence. In general, the nucleic acid probes range from about 8 to about 100 bases long, with from about 10 to about 80 bases being preferred, and from about 30 to about 50 bases being particularly preferred. That is, generally whole genes are not used. In some embodiments, much longer nucleic acids can be used, up to hundreds of bases.

In a preferred embodiment, more than one probe per sequence is used, with either overlapping probes or probes to different sections of the target being used. That is, two, three, four or more probes, with three being preferred, are used to build in a redundancy for a particular target The probes can be overlapping (i.e. have some sequence in common), or separate.

As will be appreciated by those in the art, nucleic acids can be attached or immobilized to a solid support in a wide variety of ways. By "immobilized" and grammatical equivalents herein is meant the association or binding between the nucleic acid probe and the solid support is sufficient to be stable under the conditions of binding, washing, analysis, and removal as outlined below. The binding can be covalent or non-covalent. By non-covalent binding and grammatical equivalents herein is meant one or more of either electrostatic, hydrophilic, and hydrophobic interactions. Included in non-covalent binding is the covalent attachment of a molecule, such as, sreptavidin to the support and the non-covalent binding of the biotinylated probe to the streptavidin. By covalent bindings and grammatcal equivalents herein is meant that the two moieties, the solid support and the probe, are attached by at least one bond, including sigma bonds, pi bonds and coordination bonds. Covalent bonds can be formed directly between the probe and the solid support or can be formed by a cross linker or by inclusion of a specific reactive group on either the solid support or the probe or both molecules. Immobiliation may also involve a combination of covalent and non-covalent interactions.

In general, the probes are attached to the biochip in a wide variety of ways, as will be appreciated by those in the art. As described herein, the nucleic acids can either be synthesized first, with subsequent attachment to the biochip, or can be directly synthesized on the biochip.

The biochip comprises a suitable solid substrate. By "substrate" or "solid support" or other grammatical equivalents herein is meant any material that can be modified to contain discrete individual sites appropriate for the attachment or association of the nucleic acid probes and is amenable to at least one detection method. As will be appreciated by those in the art, the number of possible substrates are very large, and include, but are not limited to, glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses, plastics, etc. In general, the substrates allow optical detection and do not appreciably fluoresce. A preferred substrate is described in copending application entitled Reusable Low Fluorescent Plastic Biochip filed Mar. 15, 1999, herein incorporated by reference in its entirety.

Generally the substrate is planar, although as will be appreciated by those in the art other configurations of substrates may be used as well. For example, the probes may be placed on the inside surface of a tube, for flow-through sample analysis to minimize sample volume. Similarly, the substrate may be flexible, such as a flexible foam, including closed cell foams made of particular plastics.

In a preferred embodiment, the surface of the blochip and the probe may be derivatized with chemical functional groups for subsequent attachment of the two. Thus, for example, the biochip is derivatized with a chemical functional group including, but not limited to, amino groups, carboxy groups, oxo groups and thiol groups, with amino groups being particularly preferred. Using these functional groups, the probes can be attached using functional groups on the probes. For example, nucleic acids containing amino groups can be attached to surfaces comprising amino groups, for example using linkers as are known in the art for example, homo-or hetero-bifunctional linkers as are well known (see 1994 Pierce Chemical Company catalog, technical section on cross inkers, pages 155–200, incorporated herein by reference). In addition, in some cases, additional linkers, such as alkyl groups (including substituted and heteroalkyl groups) may be used.

In this embodiment, the oligonudeotides are synthesized as is known in the art, and then attached to the surface of the solid support. As will be appreciated by those skilled in the art, either the 5' or 3' terminus may be attached to the solid support, or attachment may be via an internal nucleoside.

In an additional embodiment, the immobilization to the solid support may be very strong, yet non-covalent. For example, biotinylated oligonuclootides can be made, which bind to surfaces covalently coated with streptavidin, resulting in attachment.

Alternatively, the oligonucleotides may be synthesized on the surface, as is known in the art. For example, photoaclivadon techniques utrzing photopolymenrzabon compounds and techniques are used. In a preferred embodiment, the nucleic acids can be synthesized in situ, using well known photolithographic techniques, such as those described in WO 95/25116; WO 95/35505; U.S. Pat. Nos. 5,700,637 and 5,445,934; and references cited within, all of which are expressly incorporated by reference; these methods of attachment form the basis of the Affimetrix GeneChip™ technology.

In a preferred embodiment, breast cancer nucleic acids encoding breast cancer proteins are used to make a variety of expression vectors to express breast cancer proteins which can then be used in screening assays, as described below. The expression vectors may be either self-replicating extrachromosomal vectors or vectors which integrate into a host genome. Generally, these expression vectors include transcriptional and translational regulatory nucleic acid operably linked to the nucleic acid encoding the breast cancer protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid Well generally be appropriate to the host cell used to express the breast cancer protein; for example, transcriptional and translational regulatory nucleic acid sequences from Bacillus are preferably used to express the breast cancer protein in Bacillus. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression, vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for. integrating vectors are well known in the art In addition, In a preferred embodiment, the expression vector contains a selectable marker gene to allow the selection of transformed host cells. Selection genes are well known in the art and will vary with the host cell used.

The breast cancer proteins of the present invention are produced by culturing a host cell transformed with an expression vector containing nucleic acid encoding a breast cancer protein, under the appropriate conridrons to induce or cause expression of the breast cancer protein. The conditions appropriate for breast cancer protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing, of the harvest is important. For example, the baculoviral systems used in insect cell expression are lytic viruses, and thus harvest time selection can be crucial for product yield.

Appropriate host cells include yeast, bacteria, archaebacteria, fungi, and insect and animal cells, including mammalian cells. Of particular interest are *Drosophila melangester* cells, *Saccharomyces cerevisiae* and other yeasts, *E. coli, Bacillius subtillis*, Sf9 cells, C129 cells, 293 cells, Neurospora, BHK, CHO, COS, HeLa cells, THP1 cell line (a macrophage cell line) and human cells and cell lines.

In a preferred embodiment, the breast cancer proteins are expressed in mammalian cells. Mammalian expression systems are also known in the art and include retroviral systems. A preferred expression vector system is a retroviral vector system such as is generally described in PCT/US97/01019 and PCT/US97/01048, both of which are hereby expressly incorporated by reference. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter. Typically, transcription termination and polyadenylation sequences recognized by mammalian cells are regulatory regions located 3' to the translation stop codon and thus, together with the promoter elements, flank the coding sequence. Examples of transcription terminator and polyadenlyton signals include those derived form SV40.

The methods of introducing exogenous nucleic acid into mammalian hosts, as well as other hosts, is well known in the art, and will vary with the host cell used. Techniques include dextran-mediated trsnsfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, breast cancer proteins are expressed in bacterial systems. Bacterial expression systems are well known in the art. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription. In addition to a functioning promoter sequence, an efficient ribosome binding site is desirable. The expression vector may also include a signal peptide sequence that provides for secretion of the breast cancer protein in bacteria. The protein is either secreted into the grown media (gram-positive bacteria) or into the periplasmic space, located between the inner and outer membrane of the cell (gram-negative bacteria). The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanarmycin, neomycin and tetracycline. Selectable markers also include biosynthetic genes, such as those in the histidine, tryptophan and leucine biosynthetic pathways. These components are assembled into expression vectors.

Expression vectors for bacteria are well known in the art, and include vectors for *Bacillus subtills, E. coli, Streptococcus cremoris*, and *Streptococcus lividans*, among others. The bacterial expression vectors are transformed into bacterial host calls using techniques well known in the art, such as calcium chloride treatment, electroporation, and others.

In one embodiment, breast cancer proteins are produced in insect cells. Expression vectors for the transformation of insect cells, and in particular, baculovirus-based expression vectors, are well known in the art.

In a preferred embodiment, breast cancer protein is produced in yeast cells. Yeast expression systems are well known in the art, and include expression vectors for *Saccharomyces cerevisiae, Candida albicans* and *C, maltosa, Hansenula polymorpha, Kluyveromyces fragilis* and *K. lactis, Pichia guillerimondii* and *P. pastoris, Schizosaccharomyces pombe*, and *Yarrowia lipolytica*.

The breast cancer protein may also be made as a fusion protein, using techniques well known in the art. Thus, for example, for the creation of monoclonal antbodies, if the desired epitope is small, the breast cancer protein may be fused to a carrier protein to form an immunogen. Alternatively, the breast cancer protein may be made as a fusion protein to increase expression, or for other reasons. For example, when the breast cancer protein is a breast cancer peptide, the nucleic acid encoding the peptide may be linked to other nucleic acid for expression purposes.

In one embodiment, the breast cancer nucleic acids, proteins and antibodies of the invention are labeled. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the breast cancer nucleic acids, proteins and antibodies at any position. For example, the label should be capable of producing, either directly or indirectly, a detectable signal. The detectable moiety may be a radioisotope, such as $^3H$, $^{14}C$, $^{32}P$, $^{36}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the label may be employed, including those methods described by Hunter et al., *Natures* 144:945 (1962); David et al., *Biochemisty*, 13:1014(1974); Pain et al., *J. Immunol. Meth.*, 40:219(1981); and Nygren, *J. Histochem, and Cytochem.*, 30:407 (1982).

Accordingly, the present invention also provides breast cancer protein sequences. A breast cancer protein of the present invention may be identified in several ways. "Protein" in this sense includes proteins, polypeptides, and peptides. As will be appreciated by those in the art, the nucleic acid sequences of the invention can be used to generate protein sequences. There are a variety of ways to do this, including cloning the entire gene and verifying its frame and amino acid sequence, or by comparing it to known sequences to search for homology to provide a frame, assuming the breast cancer protein has homology to some protein In the database being used. Generally, the nucleic acid sequences are input into a program that will search all three frames for homology. This is done in a preferred embodiment using the following NCBI Advanced BLAST parameters. The program is blastx or blastn. The database is nr. The input data is as "Sequence in FASTA format". The organism list is "none". The "expect" is 10; the filter is default. The "descriptions" is 500, the "alignments" is 500, and the "alignment view" is pairwise. The "Query Genetic Codes" is standard (1). The matrix is BLOSUM62; gap existence cost is 11, per residue gap cost is 1; and the lambda ratio is 0.85 default. This results in the generation of a putative protein sequence.

Also included within one embodiment of breast cancer proteins are amino acid variants of the naturally occurring sequences, as determined herein. Preferably, the variants are preferably greater than about 75% homologous to the wild-type sequence, more preferably greater than about 80%, even more preferably greater than about 85% and most preferably greater than 90%. In some embodiments the homology will be as high as about 93 to 95 or 98%. As for nucleic acids, homology in this context means sequence similarity or identity, with identity being preferred. This homology will be determined using standard techniques known in the art as are outlined above for the nucleic acid homologies.

Breast cancer proteins of the present invention may be shorter or longer than the wild type amino acid sequences. Thus, in a preferred embodiment, included within the definition of breast cancer proteins are portions or fragments of the wild type sequences herein. In addition, as outlined above, the breast cancer nucleic acids of the invention may be used to obtain additional coding regions, and thus additional protein sequence, using techniques known in the art.

In a preferred embodiment, the breast cancer proteins are derivative or variant breast cancer proteins as compared to the wild type sequence. That is, as outlined more fully below, the derivative breast cancer peptide will contain at least one amino acid substitution, deletion or insertion, with amino acid substitutions being particularly preferred. The amino acid substitution, insertion or deletion may occur at any residue within the breast cancer peptide.

Also included in an embodiment of breast cancer proteins of the present invention are amino acid sequence variants. These variants fall into one or more of three classes: substitutional, insertional or deletional variants. These variants ordinarily are prepared by site specific mutagenesis of nucleotides techniques well known in the art, to produce DNA encoding the variant, and thereafter expressing the DNA in recombinant cell culture as outlined above. However, variant breast cancer protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the breast cancer protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed breast cancer variants screened for the optimal combination of desired activity. Techniques for making substitution mutations at predetermined sites in DNA having a known sequence are well known, for example, M13 primer mutagenesis and PCR mutagenesis. Screening of the mutants is done using assays of breast cancer protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the breast cancer protein are desired, substitutions are generally made in accordance with the following chart:

Chart I

| Original Residue | Exemplary Substitutions |
| --- | --- |
| Ala | Ser |
| Arg | Lys |
| Asn | Gln, His |

-continued

Chart I

| Original Residue | Exemplary Substitutions |
| --- | --- |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptde's properties are those in which (a) a hydrophilic residue, e.g. seryl or threonyl is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine The variants typically exhibit the same qualitative biological activity and will elicit the same immune response as the naturally-occurring analogue, although variants also are selected to modify the characteristics of the breast cancer proteins as needed. Alternatively, the variant may be designed such that the biological activity of the breast cancer protein is altered. For example, glycosylation sites may be altered or removed.

Covalent modifications of breast cancer polypeptides are included within the scope of this invention. One type of covalent modification includes reacting targeted amino acid residues of a breast cancer polypeptde with an organic derivatizing agent that is capable of reacting with selected side chains or the N- or C-terminal residues of a breast cancer polypeptide. Derivatization with bifunctional agents is useful, for instance, for crosslinking breast cancer to a water-insoluble support matrix or surface for use in the method for purifying anti-breast cancer antibodies or screening assays, as is more fully described below. Commonly used crosslinking agents include, e.g., 1,1-bis(diazoacetyl)-2-phonylethane, glutaraldehyde, N-hydroxysuccinimide esters, for example, esters with 4-azidosalicylic acid, homobifunctional imidoesters, including disuccinimidyl esters such as 3,3'-dithiobis(succinimidyl-proplonate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylatlon of hydroxyl groups of seryl, threonyl or tyrosyl residues, methylation of the α-amino groups of tysine, arginine, and histidine side chains [T. E. Creighton, Proteins: Structure and Molecular Properties, W. H. Freeman & Co., San Francisco, pp. 79–86 (1983)], acetylation. of the N-terminal amine, and amidation of any C-terminal carboxyl group.

Another type of covalent modification of the breast cancer polypeptide included within the scope of this invention comprises altering the native glycosylation pattern of the polypeptide. "Altering the native glycosylation pattern" is intended for purposes herein to mean deleting one or more carbohydrate moieties found in native sequence breast cancer polypeptide, and/or adding one or more glycosylation sits that are not present in the native sequence breast cancer polypeptide.

Addition of glycosylation sites to breast cancer polypeptides may be accomplished by altering the amino acid sequence thereof. The alteration may be made, for example, by the addition of, or substitution by, one or more serine or threonine residues to the native sequence breast cancer polypeptide (for O-linked glycosylation sites). The breast cancer amino acid sequence may optionally be altered through changes at the DNA level, particularly by mutating the DNA encoding the breast cancer polypeptide at preselected bases such that codons are generated that will translate into the desired amino acids.

Another means of increasing the number of carbohydrate moieties on the breast cancer polypeptide is by chemical or enzymatic coupling of glycosides to the polypeptide. Such methods are described in the art, e.g., in WO 87/05330 published 11 Sep. 1987, and in Aplin and Wriston, breast cancer Crit. Rev. Biochem., pp. 259–306 (1981).

Removal of carbohydrate moieties present on the breast cancer polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo- and exo-glycosidases as described by Thotakura et al., Moth. Enzymol., 138:350 (1987).

Another type of covalent modification of breast cancer protein, comprises lining the breast cancer polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Breast cancer polypeptides of the present invention may also be modified in a way to form chimeric molecules comprising a breast cancer polypeptide fused to another, heterologous polypeptide or amino acid sequence. In one embodiment, such a chimeric molecule comprises a fusion of a breast cancer polypeptide with a tag polypeptide which provides an epitope to which an anti-tag antibody can selectively bind. The epitope tag is generally placed at the amino- or carboxyl-terminus of the breast cancer polypeptide. The presence of such epitope-tagged forms of a breast cancer polypeptide can be detected using an antibody against the tag polypeptide. Also, provision of the epitope tag enables the breast cancer polypeptide to be readily purified by affinity purification using an anti-tag antibody or another type of affinity matrix that binds to the epitope tag. In an alternative embodiment, the chimeric molecule may comprise a fusion of a breast cancer polypeptide with an immunogiobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field at al., Mol. Cell. Biol., 82159–2165 (1988)]; the c-myc tag and the 8F9,3C7, 6E10, G4, B7 and 9E10 antibodies thereto [Evan et al., Molecular and Cellular Biology, 5:3610–3616 (1985)]; and the Herpes Simplex virus glycoprotein D (gD) tag and its antibody [Paborsky et al., Protein Engineering, 3(6):547–553 (1990)]. Other tag polypeptides include the Flag-peptide [Hopp et al., Bio Technology, 6:1204–1210 (1988)]; the KT3 epitope peptide [Martin et al., Science, 255:192–194 (1992)]; tubulin epitope peptide [Skinner et al., J. Biol. Chem., 266:15163–15166 (1991)]; and the T7 gene 10 protein peptide tag [Lutz-Freyermuth et al., Proc. Natl. Acad. Sci. USA, 87:6393–6397 (1990)].

Also included with the definition of breast cancer protein in one embodiment are other breast cancer proteins of the breast cancer family, and breast cancer proteins from other organisms, which are cloned and expressed as outlined below. Thus, probe or degenerate polymerase chain reaction (PCR) primer sequences may be used to find other related breast cancer proteins from humans or other orginisms. As will be appreciated by those in the art, particularly useful probe and/or PCR primer sequences include the unique areas of the breast cancer nucleic acid sequence. As is generally known in the art, preferred PCR primers are from about 15 to about 35 nucleotides in length, with from about 20 to about 30 being preferred, and may contain inosine as needed. The conditions for the PCR reaction are well known in the art.

In addition, as is outlined herein, breast cancer proteins can be made that are longer than those depicted in the figures, for example, by the elucidation of additional sequences, the addition of epitope or purification tags, the addition of other fusion sequences, etc.

Breast cancer proteins may also be identified as being encoded by breast cancer nucleic acids. Thus, breast cancer proteins are encoded by nucleic acids that will hybridize to the sequences of the sequence listings, or their complements, as outlined herein.

In a preferred embodiment, when the breast cancer protein is to be used to generate antibodies, for example for immunotherapy, the breast cancer protein should share at least one epitope or determinant with the full length protein. By "epitope" or "detenninant" herein is meant a portion of a protein which will generate and/or bind an antibody or T-cell receptor in the context of MHC. Thus, in is most instances, antibodies made to a smaller breast cancer protein will be able to bind to the full length protein. In a preferred embodiment, the epitope is unique, that is, antibodies generated to a unique epitope show little or no cross-reactivity.

In one embodiment, the term "anfibody" indudes antibody fragments, as are known in the art, it, including Fab, Fab$_2$, single chain antibodies (Fv for example), chimeric antibodies, etc., either produced by the modification of whole antibodies or those synttesized de novo using recombinant DNA technologies.

Methods of preparing polyclonal antbodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the BFA4 or fragment thereof or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The antibodies may, alternatively, be monoclonal antibodies. Monoclonal antibodies may be prepared using hybridoma methods, such as those described by Kohler and Milstein, Nature, 258:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent will typically include the BFA4 polypeptide Of fragment thereof or a fusion protein thereof. Generally, either peripheral blood lymphocyte ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, Monoclonal Antibodies: Principles and Practice, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphordbosyl transferase (HGPRT or HPRT), the culture medium for the hybridomas typically will include hypoxanthine, aminopterin, and thymidine ("HAT medium"), which substances prevent the growth of HGPRT-deficient cells.

In one embodiment, the antibodies are bispeciffc antibodies. Bispecific antibodies are monoclonal, preferably human or humanized, antibodies that have binding specificities for at least two different antigens. In the present case, one of the binding specificities is for the BFA4 or a fragment thereof, the other one is for any other antigen, and preferably for a cell-surface protein or receptor or receptor subunit, preferably one that is tumor specific.

In a preferred embodiment, the antibodies to breast cancer are capable of reducing or eliminating the biological function of breast cancer, as is described below. That is, the addition of anti-breast cancer antibodies (either polyclonal or preferably monoclonal) to breast cancer (or cells containing breast cancer) may reduce or eliminate the breast cancer activity. Generally, at least a 25% decrease in act is preferred, with at least about 50% being particularly preferred and about a 95–100% decrease being especially preferred.

In a preferred embodiment the antibodies to the breast cancer proteins are humanized antibodies. Humanized forms of non-human (e.g., murine) antibodies are chimeric molecules of immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522–525 (1986); Riechmann et al., *Nature*, 332:323–329 (1988); and Presta, *Curr. Op. Struct. Biol.*, 2:593–596 (1992)].

Methods for humanizing non-human antibodies are well known in the art Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., *Nature*, 321:522–525 (1986); Riechmann et al., *Nature*, 332:323–327 (1988); Verhoeyen et al., *Science*, 239:1534–1536 (1988)], by substituting rodent CDRs or CDR sequences for the corresponding sequences of a human antibody. Accordingly, such humanized antibodies are chimeric antibodies (U.S. Pat. No. 4,816, 567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.* 147(1):86–95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633, 425; 5,661,016, and in the following scientific publications: Marks et al., *Bio/Technology* 10, 779–783 (1992); Lonberg et al., *Nature* 368 856–859 (1994); Morrison, *Nature* 36 812–13 (1994); Fishwild et al., *Nature Biotechnology* 14, 845–51 (1996); Neuberger, *Nature Biotechnology* 14, 826 (1996); Lonberg and Huszar, *Interm. Rev. Immunol.* 13 65–93 (1995).

By immunotherapy is meant treatment of breast cancer with an antibody raised against breast cancer proteins. As used herein, immunotherapy can be passive or active. Passive immunotherapy as defined herein is the passive transfer of antibody to a recipient (patient). Active immunization is the induction of antibody and/or T-cell responses in a recipient (petient). Induction of an immune response is the result of providing the recipient with an antigen to which antibodies are raised. As appreciated by one of ordinary skill in the art, the antigen may be provided by injecting a polypeptide against which antibodies are desired to be raised into a recipient, or contacting the recipient with a nucleic acid capable of expressing the antigen and under conditions for expression of the antigen.

In a preferred embodiment the breast cancer proteins against Which antibodies are raised are secreted proteins as described above. Without being bound by theory, antibodies used for treatment, bind and prevent the secreted protein from binding to its receptor, thereby inactivating the secreted. breast cancer protein.

In another preferred embodiment, the breast cancer protein to Which antibodies are raised is a transmembrane protein. Without being bound by theory, antibodies used for treatrment, bind the extracellular domain of the breast cancer protein and prevent it from binding to other proteins, such as circulating ligands or cell-associated molecules. The antibody may cause down-regulation of the transmembrane breast cancer protein. As will be appreciated by one of ordinary skill in the art, the antibody may be a competitive, noncompetitive or uncompetitive inhibitor of protein binding to the extracellular domain of the breast cancer protein. The antibody is also an antagonist of the breast cancer protein. Further, the antibody prevents activation of the iransmembrane breast cancer protein. In one aspect, when the antibody prevents the binding of other molecules to the breast cancer protein, the antibody prevents growth of the cell. The antibody also sensitizes the cell to cytotoxic agents, including, but not limited to TNF-α, TNF-β, IL-1, INF-γ and IL-2, or chemotherapeutic agents including 5FU, vinblastine, actinomycin D, cisplatin, methotrexate, and the like. In some instances the antibody belongs to a sub-type that activates serum complement when complexed with the transmembrane protein thereby mediating cytotoxicity. Thus, breast cancer is treated by administering to a patient antibodies directed against the transmembrane breast cancer protein.

In another preferred embodiment, the antibody is conjugated to a therapeutic moiety. In one aspect the therapeutic moiety is a small molecule that modulates the activity of the breast cancer protein. In another aspect the therapeutic moiety modulates the activity of molecules associated with or in dose proximity to the breast cancer protein. The therapeutic moiety may inhibit enzymatic activity such as protease or protein kinase activity associated with breast cancer.

In a preferred embodiment, the therapeutic moiety may also be a cytotoxic agent in this method, targeting the cytotoxic agent to tumor tissue or cells, results in a reduction in the number of afflicted cells, thereby reducing symptoms associated with breast cancer. Cytotoxic agents are numerous and varied and include, but are not limited to, cytotoxic drugs or toxins or active fragments of such toxins. Suitable toxins and their corresponding fragments include diptheria A chain, exotoxin A chain, ricin A chain, abrin A chain, curcin, crotin, phenomycin, enomycin and the like. Cytotoxic agents also include radiochemicals made by conjugating radioisotopes to antibodies raised against breast cancer proteins, or binding of a radionuclide to a chelating agent that has been covalenlly attached to the antibody. Targeting the therapeutic moiety to transmembrane breast cancer proteins not only serves to increase the local concentration of therapeutic moiety in the breast cancer afflicted area, but also serves to reduce deleterious side effects that may be associated with the therapeutic moiety.

In another preferred embodiment, the PC protein against which the antibodies are raised is an intracellular protein. In this case, the antibody may be conjugated to a protein which facilitates entry Into the cell. In one case, the antibody enters the cell by endocytosis. In another embodiment, a nucleic acid encoding the antibody is administered to the indivdual or cell. Moreover, wherein the PC protein can be targeted within a cell, i.e., the nucleus, an antibody thereto contains a signal for that target localization, i.e., a nuclear localization signal.

The breast cancer antibodies of the invention specifically bind to breast cancer proteins. By "specifically bind" herein is meant that the antibodies bind to the, protein with a binduing constant in the range of at least $10^{-4}$ $10^{-6}M^{-1}$, with a preferred range being $10^{-7}$–$10^{-9}M^{-1}$.

In a preferred embodiment, the breast cancer protein is purified or isolated after expression. Breast cancer proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the breast cancer protein may be purified using a standard anti-breast cancer antibody column. Ultrafiltration and disaffirmation techniques, in conjunction with protein concentration, are also useful. For general guidance in suitable purification techniques, see Scopes, R., Protein Purification, Springer-Verlag, New York. (1982). The degree of purification necessary will vary depending on the use of the breast cancer protein. In some instances no purification will be necessary.

Once expressed and purified if necessary, the breast cancer proteins and nucleic acids are useful in a number of applications.

In one aspect, the expression levels of genes are deterninined for different cellular states in the breast cancer phenotype; that is, the expression levels of genes in normal breast tissue and in breast cancer tissue (and in some cases, for varying severities of breast cancer that relate to prognosis, as outlined below) are evaluated to provide expression profiles. An expression profile of a particular cell state or point of development is essentially a "fingerprint" of the state; while two states may have any particular gene similarly expressed, the evaluation of a number of genes simultaneously allows the generation of a gene expression profile that is unique to the state of the cell. By comparing expression profiles of cells in different states, information regarding which genes are important (including both up- and down-regulation of genes) in each of these states is obtained. Then, diagnosis may be done or confirmed: does tissue from a particular patient have the gene expression profile of normal or breast cancer tissue.

"Differential expression," or grammatical equivalents as used herein, refers to both qualitative as well as quantitative differences in the genes' temporal and/or cellular expression patterns within and among the cells. Thus, a breast cancer gene can qualitatively have its expression altered, including an activation or inactivation, in, for example, normal versus breast cancer tissue. That is, genes may be turned on or turned off in a particular state, relative to another state. As is apparent to the skilled artisan, any comparison of two or more states can be made. Such a qualitatively regulated gene will exhibit an expression pattern within a state or cell type which is detectable by standard techniques in one such state or cell type, but is not detectable in both. Alternatively, the determination is quantitative in that expression is increased or decreased; that is, the expression of the gene is either upregulated, resulting in an increased amount of transcript, or downregulated, resulting in a decreased amount of transcript. The degree to which expression differs need only be large enough to quantify via standard characterization techniques as outlined below, such as by use of Affymetrix GeneChip™ expression arrays, Lockhart, Nature Biotechnology, 14:1675–1680 (1996), hereby expressly incorporated by reference. Other techniques include, but are not limited to, quantitative reverse transcriptase PCR, Northern analysis and RNase protection. As outlined above, preferably the change in expression (i.e. upregulation or downregulation) is at least about 50%, more preferably at least about 100%, more preferably at least about 150%, more preferably, at least about 200%, with from 300 to at least 1000% being especially preferred.

As will be appredated by those in the art, this may be done by evaluation at either the gene transcript, or the protein level; that is, the amount of gone expression may be monitored using nucleic acid probes to the DNA or RNA equivalent of the gene transcript, and the quantification of gene expression levels, or, alternatively, the final gene product itself (protein) can be monitored, for example through the use of antibodies to the breast cancer protein and standard immunoassays (ELISAs,e tc.) or other techniques, including mass spectroscopy assays, 2D gel electrophoresis assays, etc. Thus, the proteins corresponding to breast cancer genes, i.e. those identified as being important in a breast cancer phenotype, can be evaluated in a breast cancer diagnostic test In a preferred embodiment, gene expression monitoring is done and a number of genes, i.e. an expression profile, is monitored simultaneously, although multiple protein expression monitoring can be done as well. Similarly, these assays may be done on an individual basis as well.

In this embodiment, the breast cancer nucleic acid probes are attached to biochips as outlined herein for the detection and quantification of breast cancer sequences in a particular cell. The assays are further described below in the example.

In a preferred embodiment nucleic acids encoding the breast cancer protein are detected. Although DNA or RNA encoding the breast cancer protein may be detected, of particular interest are methods wherein the mRNA encoding a breast cancer protein is detected. The presence of mRNA in a sample is an indication that the breast cancer gene has been transcribed to form the mRNA, and suggests that the protein is expressed. Probes to detect the mRNA can be any nucleotide/deoxynucleotide probe that is complementary to and base pairs with the mRNA and includes but is not limited to oligonucleotides, cDNA or RNA. Probes also should contain a detectable label, as defined herein. In one method the mRNA is detected after immobilizing the nucleic acid to be examined on a solid support such as nylon membranes and hybridizing the probe w the sample. Following washing to remove the non-specifically bound probe, the label is detected in another method detection of the mRNA is performed in situ. In this method permeabilized cells,or tissue samples are contacted with a detectably labeled nucleic acid probe for sufficient time to allow the probe to hybridize with the target mRNA. Following washing to remove the non-specifically bound probe, the label is detected. For example a digoxygenin labeled riboprobe (RNA probe) that is, complementary to the mRNA encoding a breast cancer protein is detected by binding the digoxygenin with an anti-digoxygenin secondary antibody and developed with nitro blue totrazolium and 5-bromo-4-chloro-3-indoyl phosphate.

In a preferred embodiment, any of the three classes of proteins as described herein (secreted, transmembrane or intracellular proteins) are used in diagnostic assays. The breast cancer proteins, antibodies, nucleic acids, modified proteins and cells containing breast cancer sequences are used in diagnostic assays. This can be done on an individual gene or,corresponding polypeptide level. In a preferred embodiment, the expression profiles are used, preferably in conjunction with high throughput screening techniques to allow monitoring for expression profile genes and/or corresponding potypeptides.

As described and defined herein, breast cancer proteins, including intracellular, transmembrane or secreted proteins, find use as markers of breast cancer. Detection of these proteins in putative breast cancer tissue of patients allows for a determination or diagnosis of breast cancer. Numerous methods known to those of ordinary skill in the art find use in detecting breast cancer. In one embodiment, antibodies are used to detect breast cancer proteins. A preferred method separates proteins from a sample or patient by electrophoresis on a gel (typically a denaturing and reducing protein gel, but may be any other type of gel including isoelectric focusing gels and the like). Following separation of proteins, the breast cancer protein is detected by immunoblotting with antibodies raised against the breast cancer protein. Methods of immunoblotting are well known to those of ordinary skill in the art.

In another preferred method, antbodies to the breast cancer protein find use in in situ imaging techniques. In this method cells are contacted with from one to many antibodies to the breast cancer protein(s). Following washing to remove nonspecific antibody,binding, the presence of the antibody or antibodies is detected. In one embodiment the antibody is detected by incubating with a secondary antibody that contains a detectable label. In another method the primary antibody to the breast cancer protein(s) contains a detectable label. In another preferred embodiment each one of multiple primary antibodies contains a distinct and detectable label. This method finds particular use in simultaneous screening for a pluralilty of breast cancer proteins. As will be appreciated by one of ordinary skill in the art, numerous other histological imaging techniques are useful in the invention.

In a preferred embodiment the label is detected in a fluorometer which has the ability to detect and distinguish emissions of different wavelengths. In addition, a fluorescence activated cell sorter (FACS) can be used in the method.

In another preferred embodiment, antibodies find use in diagnosing breast cancer from blood samples. As previously described, certain breast cancer proteins are secreted/circulating molecules. Blood samples, therefore, are useful as samples to be probed or tested for the presence of secreted breast cancer proteins. Antibodies can be used to detect the breast cancer by any of the previously described immunoassay techniques including ELISA, immunoblotting (Western blotting), immunoprecipitation, BIACORE technology and the like, as will be appreciated by one of ordinary skill in the art.

In a preferred embodiment, in situ hybridization of labeled breast cancer nucleic acid probes to tissue arrays is done. For example, arrays of tissue samples, Including breast cancer tissue and/or normal tissue, are made. In situ hybridization as is known in the art can then be done.

It is understood that when comparing the fingerprints between an individual and a standard, the skilled artisan can make a diagnosis as well as a prognosis. It is further understood that the genes which indicate the diagnosis may differ from those which indicate the prognosis.

In a preferred embodiment, the breast cancer proteins, antibodies, nucleic acids, modified proteins and cells containing breast cancer sequences are used in prognosis assays. As above, gene expression profiles can be generated that correlate to breast cancer severity, In terms of long term prognosis. Again, this may be done on either a protein or gene level, with the use of genes being preferred. As above, the breast cancer probes are attached to biochips for the detection and quantification of breast cancer sequences in a tissue or patient The assays proceed as outlined for diagnosis.

In a preferred embodiment, any of the three classes of protein's as described herein are used in drug screening assays. The breast cancer proteins, antbodies, nucleic acids, modified proteins and cells containing breast cancer sequences are used in drug screening assays or by evaluating the effect of drug candidates on a "gone expression profile" or expression profile of polypeptides. In a preferred embodiment, the expression profiles are used, preferably in conjunction with high throughput screening techniques to allow monitoring for expression profile genes after treatment with a candidate agent, Zlokarnik, et al., Science 279, 84–8 (1998), Heid, 1996#69.

In a preferred embodiment, the breast cancer proteins, antibodies, nucleic acids, modified proteins and cells containing the native or modified breast cancer proteins are used in screening assays. That is, the present invention provides novel methods for screening for compositions which modulate the breast cancer phenotype. As above, this can be done on an individual gene level or by evaluating the effect of drug candidates on a "gene expression profile". In a preferred embodiment expression profiles are used, preferably in conjunction with high throughput screening techniques to allow monitoring for expression profile genes after treatment with a candidate agent, see Zlokarnik, supra.

Having identified the breast cancer genes herein, a variety of assays may be executed. In a preferred embodiment, assays may be run on an individual gene or protein level. That is, having identified a particular gene as up regulated in breast cancer, candidate bioactive agents may be screened to modulate this gene's response; preferably to down regulate the gene, although in some circumstances to up regulate the gene. "Modulation" thus includes both an increase and a decrease in gene expression. The preferred amount of modulation will depend on the original change of the gene expression in normal versus tumor tissue, with changes,of at least 10%, preferably 50%, more preferably 100–300%, and in some embodiments 300–1000% or greater. Thus, if a gene exhibits a 4 fold increase in tumor compared to normal tissue, a decrease of about four told is desired; a 10 fold decrease in tumor compared to normal tissue gives a 10 fold increase in expression for a candidate agent is desired.

As will be appreciated by those in the art, this may be done by evaluation at either the gene or the protein level; that is, the amount of gene expression may be monitored using nucleic acid probes and the quantification of gene expression levels, or, alternatively, the gene product itself can be monitored, for example through the use of antibodies to the breast cancer protein and standard immunoassays.

In a preferred embodiment, gene expression monitoring is done and a number of genes, i.e. an expression profile, is monitored simultaneously, although multiple protein expression monitoring can be done as well.

In this embodiment, the breast cancer nucleic acid probes are attached to biochips as outlined herein for the detection and quantification of breast cancer sequences in a particular cell. The assays are further described below.

Generally, in a preferred embodiment, a candidate bioactive agent is added to the cells prior to analysis. Moreover, screens are provided to identify a candidate bioactive agent which modulates breast cancer, modulates breast cancer proteins, binds to a breast cancer protein, or interferes between the binding of a breast cancer protein and an antibody.

The tern "candidate bioactive agent" or "drug candidate" or grammatical equivalents as used herein describes any molecule, e.g., protein, oligopeptide, small organic molecule, polysaccharide, polynucleotide, etc., to be tested for bioactive agents that are capable of directly or indirectly altering the breast cancer phenotype or the expression of a breast cancer sequence. Including both nucleic acid sequences and protein sequences. In preferred embodiments, the bioactive agents modulate the expression profiles, or expression profile nucleic acids or proteins provided herein. In a particularly preferred embodiment, the candidate agent suppresses a breast cancer phenotype, for example to a normal breast tissue fingerprint. Similarly, the candidate agent preferably suppresses a severe breast cancer phenotype. Generally a pluralilty of assay mixtures are run in parallel with different agent concentrations to obtain a differential response to the various concentrations. Typically, one of these concentrations serves as a negative control, i.e., at zero concentration or below the level of detection.

In one aspect, a candidate agent will neutralize the effect of a CRC protein. By "neutralize" is meant that activity of a protein is either inhibited or counter acted against so as to have substantially no effect on a cell.

Candidate agents encompass numerous chemical classes, though typically they are organic molecules, preferably small organic compounds having a molecular weight of more than 100 and less than about 2,500 daltons. Preferred small molecules are less than 2000, or less than 1500 or less than 1000 or less than 500 D. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, dervatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, the candidate bioactive agents are proteins. By "protein" herein is meant at least two covalently attached amino acids, which includes proteins, potypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The, side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In a preferred embodiment, the candidate bioactive agents are naturally occurring proteins or fragments of naturally occurring proteins. Thus, for example, cellular extracts containing proteins, or random or directed digests of proteinaceous cellular extracts may be used. In this way libraries of procaryotic and eucaryotic proteins may be made for screening in the methods of the invention. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of nucleic acid binding domains, the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids, as defined above.

As described above generally for proteins, nucleic acid candidate bioactive agents may be naturally occurring nucleic acids, random nucleic acids, or "biased" random nucleic acids. For example, digests of procaryotic or eucaryotic genomes may be used as is outlined above for proteins.

In a preferred embodiment, the candidate bioactive agents are organic chemical moieties, a wide variety of which are available in the literature.

After the candidate agent has been added and the cells allowed to incubate for some period of time, the sample containing the target sequences to be analyzed is added to the biochip. If required, the target sequence is prepared using known techniques. For example, the sample may be treated to lyse the cells, using known lysis buffers, electroporation, etc., with purification and/or amplification such as PCR occurring as needed, as will be appreciated by those in the art. For example, an in vitro transcription with labels covalently attached to the nucleosides is done. Generally, the nucleic acids are labeled with biotin-FITC or PE, or with cy3 or cy5.

In a preferred embodiment, the target sequence is labeled with, for example, a fluorescent, a chemiluminescent, a chemical, or a radioactive signal, to provide a means of detecting the target sequence's specific binding to a probe. The label also can be an enzyme, such as, alkaline phosphatase or horseradish peroxidase, which when provided with an appropriate substrate produces a product that can be detected. Alternatively, the label can be a labeled compound or small molecule, such as an enzyme inhibitor, that binds but is not catalyzed or, altered by the enzyme. The label also can be a moiety or compound, such as, an epitope tag or biotin which specifically binds to streptavidin. For the example of biotin, the streptavidin is labeled as described above, thereby, providing a detectable signal for the bound target sequence. As known in the art, unbound labeled streptavidin is removed prior to analysis.

As will be appreciated by those in the art, these assays can be direct hybridization assays or can comprise "sandwich assays", which include the use of multiple probes, as is generally outlined in U.S. Pat. Nos. 5,681,702, 5,597,909, 5,545,730, 5,594,117, 5,591,584, 5,571,670, 5,580,731, 5,571,670, 5,591,584, 5,624,802, 5,635,352, 5,594,118, 5,359,100, 5,124,246 and 5,681,697, all of which are hereby incorporated by reference. In this embodiment, in general, the target nucleic acid is prepared as outlined above, and then added to the biochip comprising a plurality of nucleic acid probes, under conditions that allow the formation of a hybridization complex.

A variety of hybridization conditions may be used in the present invention, including high, moderate and low stringency conditions as outlined above. The assays are generally run under stringency conditions which allows formation of the label probe hybridization complex only in the presence of target Stringency can be controlled by altering a step parameter that is a thermodynamic variable, including, but not limited to, temperature, formamide concentration, salt concentration, chaotropic salt concentration pH, organic solvent concentration, etc.

These parameters may also be used to control non-specific binding, as is generally outlined in U.S. Pat. No. 5,681,697. Thus it may be desirable to perform certain steps at higher stringency conditions to reduce non-specific binding.

The reactions outlined herein may be accomplished in a variety of ways, as will be appredated by those in the art. Components of the reaction may be added simultaneously, or sequentially, in any order, with preferred embodiments outlined below. In addition, the reaction may include a variety of other reagents may be included in the assays. These include reagents like salts, buffers, neutral proteins, e.g. albumin, detergents, etc which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target.

Once the assay is run, the data is analyzed to determine the expression levels, and changes in expression levels as between states, of individual genes, forming a gene expression profile.

The screens are done to identify drugs or bioactive agents that modulate the breast cancer phenotype. Specifically, there are several types of screens that can be run. A preferred embodiment is in the screening of candidate agents that can induce or suppress a particular expression profile, thus preferably generating the associated phenotype. That is, candidate agents that can mimic or produce an expression profile in breast cancer similar to the expression profile of normal breast tissue is expected to result in a suppression of the breast cancer phenotype. Thus, in this embodiment, mimicking an expression profile, or changing one profile to another, is the goal.

In a preferred embodiment, as for the diagnosis and prognosis applications, having identified the breast cancer genes important in any one state, screens can be run to alter the expression of the genes individually. That is, screening for modulation of regulation of expression of a single gene can be done; that is, rather than try to mimic all or part of an expression profile, screening for regulation of individual genes can be done. Thus, for example, particularly in the case of target genes whose presence or absence is unique between two states, screening is done for modulators of the target gene expression.

In a preferred embodiment, screening is done to alter the biological function of the expression product of the breast cancer gene. Again, having identified the importance of a gene in a particular state, screening for agents that bind and/or modulate the biological activity of the gene product can be run as is more fully outlined below.

Thus, screening of candidate agents that modulate the breast cancer phenotype either at the gene expression level or the protein level can be done.

In addition screens can be done for novel genes that are induced in response to a candidate agent. After identifying a candidate agent based upon its ability to suppress a breast cancer expression pattern leading to a normal expression pattern, or modulate a single breast cancer gene expression profile so as to mimic the expression of the gene from normal tissue, a screen as described above can be performed to identify genes that are specifically modulated in response to the agent. Comparing expression profiles between normal tissue and agent treated breast cancer tissue reveals genes that are not expressed in normal breast tissue or breast cancer tissue, but are expressed in agent treated tissue. These agent specific sequences can be identified and used by any of the methods described herein for breast cancer genes or proteins. In particular these sequences and the proteins they encode find use in marking or identifying agent treated cells. In addition, antibodies can be raised against the agent induced proteins and used to target novel therapeutics to the treated breast cancer tissue sample.

Thus, In one embodiment, a candidate agent is administered to a population of breast cancer cells, that thus has an associated breast cancer expression profile. By "administration" or "contacting" herein is meant that the candidate agent is added to the cells n such a manner as to allow the agent to act upon the cell, whether by uptake and intracellular action, or by action at the cell surface. In some embodiments, nucleic acid encoding a proteinaceous candidate agent i.e. a peptide) may be put into a viral construct such as a retroviral construct and added to the cell, such that expression of the peptide agent is accomplished; see PCT US97/01019, hereby expressly incorporated by reference.

Once the candidate agent has been administered to the cells, the cells can be washed if desired and are allowed to incubate under preferably physiological conditions for some period of time. The cells are then harvested and a new gene expression profile is generated, as outlined herein.

Thus, for example, breast cancer tissue may be screened for agents that reduce or suppress the breast cancer phenotype. A change in at least one gene of the expression profile indicates that the agent has an effect on breast cancer activity. By defining such a signature for the breast cancer phenotype, screens for new drugs that alter the phenotype can be devised. With this approach, the drug target need not be known and need not be represented in the original expression screening platform, nor does the level of transcript for the target protein need to change.

In a preferred embodiment, as outlined above, screens may be done on individual genes and gene products (proteins). That is, having identified a particular breast cancer gene as important in a particular state, screening of modulators of either the expression of the gene or the gene product itself can be done. The gene products of breast cancer genes are sometimes referred to herein as "breast cancer proteins" or "breast cancer modulating proteins" or "BCMP". Additionally, "modulator" and "modulating" proteins are sometimes used interchangeably herein. In one embodiment the breast cancer protein is termed BFA4. BFA4 sequences can be identified as described herein for breast cancer sequences. In one embodiment, a BFA4 protein sequence is as depicted in FIG. 2 (SEQ ID NO2). The breast cancer protein may be a fragment, or aliernatively, be the full length protein to the fragment shown herein. Preferably, the breast cancer protein is a fragment in a preferred embodiment, the amino acid sequence which is used to determine sequence identity or similarity is that depicted in FIG. 2. In another embodiment, the sequences are naturally occurring allelic variants of a protein having the sequence depicted in FIG. 2. In another embodiment, the sequences are sequence variants as further described herein.

Preferably, the breast cancer protein is a fragment of approximately 14 to 24 amino acids long. More preferably the fragment is a soluble fragment. Preferably, the fragment includes a non-transmembrane region. In a preferred embodiment, the fragment has an N-terminal Cys to aid in solubility. In one embodiment, the c-terminus of the fragment is kept as a free acid and the n-terminus is a free amine to aid in coupling, i.e., to cysteine. Preferably, the fragment of approximately 14 to 24 amino acids long. More preferably the fragment is a soluble fragment, in another embodiment, a BFA4 fragment has at least one BFA4 bioactivitly as defined below.

In one embodiment the breast cancer proteins are conjugated to an immunogenic agent as discussed herein. In one embodiment the breast cancer protein is conjugated to BSA.

Thus, in a preferred embodiment, screening for modulators of expression of specific genes can be done. This will be done as outlined above, but in general the expression of only one or a few genes are evaluated.

In a preferred embodiment, screens are designed to first find candidate agents that can bind to breast cancer proteins, and then these agents may be used in assays that evaluate the ability of the candidate agent to modulate breast cancer activity. Thus, as will be appreciated by those in the art, there are a number of different assays which may be run; binding assays and actively assays.

In a preferred embodiment, binding assays are done. In general, purified or isolated gene product is used; that is, the gene products of one or more breast cancer nucleic acids are made. In general, this is done as is known in the art. For example, antibodies are generated to the protein gene products, and standard immunoassays are run to determine the amount of protein present. Alternatively, cells comprising the breast cancer proteins can be used in the assay.

Thus, In a preferred embodiment, the methods comprise combining a breast cancer protein and a candidate bioactive agent, and determining the binding of the candidate agent to the breast cancer protein. Preferred embodiments utilize the human breast cancer protein, although other mammalian proteins may also be used, for example for the development of animal models of human disease. In some embodiments, as outlined herein, variant or derivative breast cancer proteins may be used.

Generally, in a preferred embodiment of the methods herein, the breast cancer protein or the candidate agent is non-diffusably bound to an insoluble support having isolated sample receiving areas (e.g. a microtiter plate, an array, etc.). It is understood that aliematively, soluble assays known in the art may be performed. The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, teflon™, etc. Microtiter plates and arrays are especially convenient because a large number of assays can be carried out simultaneously, using small amounts of reagents and samples. The particular manner of binding of the composition is not crucial so long as it is compatible with the reagents and overall methods of the invention, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous, protein or other moiety.

In a preferred embodiment, the breast cancer protein is bound to the support, and a candidate bioactive agent is added to the assay. Alternatively, the candidate agent is bound to the support and the breast cancer protein is added. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, functional assays (phosphorylation assays; etc.) and the like.

The determination of the binding of the candidate bioactive agent to the breast cancer protein may be done in a number of ways. In a preferred embodiment, the candidate bioactive agent is labelled, and binding determined directly. For example, this may be done by attaching all or a portion of the breast cancer protein to a solid support, adding a labelled candidate agent (for example a fluorescent label), washing off excess reagent, and determining whether the label is present on the solid support. Various blocking and washing steps may be utilized as is known in the art.

By "labeled" herein is meant that the compound is either directly or indirectly labeled with a label which provides a detectable signal, e.g. radioisotope, fluorescers, enzyme, antibodies, particles such as magnetic particles, chemiluminescers, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the proteins (or proteinaceous candidate agents) may be labeled at tyrosine positions using $^{125}$I, or with fluorophores. Alternatively, more than one component may be labeled with different labels; using $^{125}$I for the proteins, for example, and a fluorophor for the candidate agents.

In a preferred embodiment, the binding of the candidate bioactive agent is determined through the use of competitive binding assays. In this embodiment, the competitor is a binding moiety known to bind to the target molecule (i.e. breast cancer), such as an antibody, peptide, binding partner, ligand, etc. Under certain circumstances, there may be competitive binding as between the bioactive agent and the binding moiety, with the binding moiety displacing the bioactive agent.

In one embodiment, the candidate bioactive agent is labeled. Either the candidate bioactive agent, or the competitor, or both, is added first to the protein for a time sufficient to allow binding, if present Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient Excess reagent is generally removed or washed away. The second component is then added, and the presence or absence of the labeled component is followed, to indicate binding.

In a preferred embodiment, the competitor is added first, followed by the candidate bioactive agent. Displacement of the competitor is an indication that the candidate bioactive agent is binding to the breast cancer protein and thus is capable of binding to, and potentially modulating, the activity of the breast cancer protein. In this embodiment, either component can be labeled. Thus, for example, if the competitor is labeled, the presence of label in the wash solution indicates displacement by the agent Alternatively, if the candidate bioactive agent is labeled, the presence of the label on the support indicates displacement.

In an alternative embodiment, the candidate bioactive agent is added first, with incubation and washing, followed by the competitor. The absence of binding by the competitor may indicate that the bioactive agent is bound to the breast cancer protein with a higher affinity. Thus, if the candidate bioactive agent is labeled, the presence of the label on the support, coupled with a lack of competitor binding, may indicate that the candidate agent is capable of binding to the breast cancer protein.

In a preferred embodiment the methods comprise differential screening to identity bioactive agents that are capable of modulating the activity of the breast cancer proteins. In this embodiment, the methods comprise combining a breast cancer protein and a competitor in a first sample. A second sample comprises a candidate bioactive agent, a breast cancer protein and a competitor. The binding of the competitor is determined for both samples, and a change, or difference in binding between the two samples indicates the presence of an agent capable of binding to the breast cancer protein and potentially modulating its activity. That is, if the binding of the competitor is different in the second sample relative to the first sample, the agent is capable of Ending to the breast cancer protein.

Alternatively, a preferred embodiment utilizes differential screening to identify drug candidates that bind to the native breast cancer protein, but cannot bind to modified breast cancer proteins. The structure of the breast cancer protein may be modeled, and used in rational drug design to synthesize agents that interact with that site. Drug candidates that affect breast cancer bioactivitly are also identified by screening drugs for the ability to either enhance or reduce the activity of the protein.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Screening for agents that modulate the activity of breast cancer proteins may also be done. In a preferred embodiment, methods for screening for a bioactive agent capable of modulating the activity of breast cancer proteins comprise the steps of adding a candidate bioactive agent to a sample of breast cancer proteins, as above, and determining an alteration in the biological activity of breast cancer proteins. "Modulating the activity" of breast cancer includes an increase in activity, a decrease in activity, or a change in the type or kind of activity present. Thus, in this embodiment, the candidate agent should both bind to breast cancer proteins (although this may not be necessary), and alter its biological or biochemical activity as defined herein. The methods include both in vitro screening methods, as are generally outlined above, and in vivo screening of cells for alterations in the presence, distribution, activity or amount of breast cancer proteins.

Thus, in this embodiment, the methods comprise combining a breast cancer sample and a candidate bioactive agent, and evaluating the effect on breast cancer activity. By "breast cancer activity" or grammatical equivalents herein is meant at least one of breast cancer's biological activities, including, but not limited to, cell division, preferably in breast tissue, dell proliferation, tumor growth and transformation of cells. In one embodiment, breast cancer, activity includes activation of BFA4 or a substrate thereof by BFA4. An inhibitor of breast cancer activity is an agent which inhibits any one or more breast cancer activities.

In a preferred embodiment, the activity of the breast cancer protein is increased; in another preferred embodiment, the activity of the breast cancer protein is decreased. Thus, bioactive agents that are antagonists are preferred in some embodiments, and bioactive agents that are agonists may be preferred in other embodiments.

In a preferred embodiment, the invention provides methods for screening for bioactive agents capable of modulating the activity of a breast cancer protein. The methods comprise adding a candidate bioactive agent, as defined above, to a cell comprising breast cancer proteins. Preferred cell types include almost any cell. The cells contain a recombinant nucleic acid that encodes a breast cancer protein. In a preferred embodiment a library of candidate agents are tested on a plurality of cells.

In one aspect, the assays are evaluated in the presence or absence or previous or subsequent exposure of physiological signals, for example hormones, antibodies, peptides, antigens, cytokines, growth factors, action potentials, pharmacological agents including chemotherapeutics, radiation, carcinogenics, or other cells (i.e. cell-cell contacts). In another example, the determinations are determined at different stages of the cell cycle process.

In this way, bioactive agents are identified. Compounds with, pharmacological activity are able to enhance or interfere with the activity of the breast cancer protein. In one embodiment, "breast cancer protein activity" as used herein includes at least one of the following: breast cancer activity, transcription factor activity, binding to BFA4, activation of BFA4 or activation of substrates of BFA4 by BFA4. An inhibitor of BFA4 inhibits at least one of BFA4's bioactivies.

In one embodiment, a method of inhibiting breast cancer cell division is provided. The method comprises administration of a breast cancer inhibitor.

In another embodiment, a method of inhibiting breast tumor growth is provided. The method comprises administration of a breast cancer inhibitor. In a preferred embodiment, the inhibitor is an inhibitor of BFA4.

In a further embodiment, methods of treating cells or individuals with breast cancer are provided. The method comprises administration of a breast cancer inhibitor. In a preferred embodiment, the inhibitor is an inhibitor of BFA4.

In one embodiment, a breast cancer inhibitor is an antibody as discussed above. In another embodiment, the breast cancer inhibitor is an antisense molecule. Antisense molecules as used herein include antisense or sense oligonucleotides comprising a singe-stranded nucleic acid sequence (either RNA or DNA) capable of binding to target mRNA (sen se) or DNA (antisense) sequences for breast cancer molecules. A preferred antisense molecule is for BFA4 or for a ligand or activator thereof. Antisense or sense oligonucleotides, according to the present invention, comprise a fragment generally at least about 14 nucleotides, preferably from about 14 to 30 nucleotides. The ability to derive an antisense or a sense oligonucleotide, based upon a cDNA sequence encoding a given protein is described in, for example Stein and Cohen (*Cancer Res.* 48:2659, 1988) and van der Krol et al. (*Bio Techniques* 6:958, 1988).

Antisense molecules may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell. Alternatively, a sense or an antisense oligonucleotide may be introduced into a cell containing the target nucleic acid sequence by formation of an oligonucleotide-lipid complex, as described in WO 90/10448. It is understood that the use of antisense molecules or knock out and knock in models may also be used in screening assays as discussed above, in addition to methods of treatment The compounds having the desired pharmacological activity may be administered in a physiologically acceptable carrier to a host, as previously described. The agents may be administered in a variety of ways, orally, parenterally e.g., subcutaneously, intraperitoneally, intravascularly, etc. Depending upon the manner of introduction, the compounds may be formulated in a variety of ways. The concentration of therapeutically active compound in the formulation may vary from about 0.1–100 wt. %. The agents may be administered alone or in combination with other treatments, i.e., radiation.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for, securing an adequate pH value, and skin penetration enhancers can be used as auxiliary agents.

Without being bound by theory, it appears that the various breast cancer sequences are important in breast cancer. Accordingly, disorders based on mutant or variant breast cancer genes may be determined. In one embodiment, the invention provides methods for identifying cells containing variant breast cancer genes comprising determining all or part of the sequence of at least one endogeneous breast cancer gene in a cell. As will be appreciated by those in the art, this may be done using any number of sequencing techniques. In a preferred embodiment the invention provides methods of identifying the breast cancer genotype of an individual comprising determining all or part of the sequence of at least one breast cancer gene of the individual. This is generally done in at least one tissue of the individual, and may include the evaluation of a number of tissues or different samples of the same tissue. The method may include comparing the sequence of the sequenced gene to a known gene, i.e. a wild-type gene.

The sequence of all or part of the breast cancer gene can then be compared to the sequence of a known breast cancer gene to determine if any differences exist. This can be done using any number of known homology programs, such as Bestfit, etc. In a preferred embodiment, the presence of a difference in the sequence between the breast cancer gene of the patient and the known breast cancer gene is indicative of a disease state or a propensity for a disease state, as outlined herein.

In a preferred embodiment, the breast cancer genes are used as probes to determine the number of copies of the breast cancer gene in the genome.

In another preferred embodiment breast cancer genes are used as probed to determine the chromosomal localization of the breast cancer genes. Information such as chromosomal localization finds use in providing a diagnosis or prognosis in particular when chromosomal abnormalities such as translocations, and the like are identified in breast cancer gene loci.

Thus, in one embodiment, methods of modulating breast cancer in cells or organisms are provided. In one embodiment, the methods comprise administering to a cell an antibody that reduces or eliminates the biological activity of an endogenous breast cancer protein. Alternatively, the methods comprise administering to a cell or organism a recombinant nucleic acid encoding a breast cancer protein. As will be appreciated by those in the art, this may be accomplished in any number of ways. In a preferred embodiment, for example when the breast cancer sequence is down-regulated in breast cancer, the activity of the breast cancer gene is increased by, increasing the amount in the cell, for example by overexpressing the endogenous protein or by administering a gene encoding the sequence, using known gene-therapy techniques, for example. In a preferred embodiment, the gene therapy techniques include the incorporation of the exogenous gene using enhanced homologous recombination (EHR), for example as described in PCT/US93/03868, hereby incorporated by reference in its entirety. Alternatively, for example when the breast cancer sequence is up-regulated in breast cancer, the activity of the endogeneous gene is decreased, for example by the administration of an inhibitor of breast cancer, such as an antisense nucleic acid.

In one embodiment, the breast cancer proteins of the present invention may be used to generate polyclonal and monoclonal antibodies to breast cancer proteins, which are useful as described herein. Similarly, the breast cancer proteins can be coupled, using standard technology, to affinity chromatography columns. These columns may then be used to purify breast cancer antibodies. In a preferred embodiment, the antibodies are generated to epitopes unique to a breast cancer protein; that is, the antibodies show little or no cross-reactivity to other pmteins. These antibodies find use in a number of applications. For example, the breast cancer antibodies may be coupled to standard affinity chromatography columns and used to purify breast cancer proteins. The antibodies may also be used as blocking polypeptides, as outlined above, since they will specifically bind to the breast cancer protein.

In one embodiment, a therapeutically effective dose of a breast cancer or modulator thereof is administered to a patient By "therapeutically effective dose" herein is meant a dose that produces the effects for which it is administered. The exact dose will depend on the purpose of the treatment, and will be ascertainable by one skilled in the art using known techniques. As is known in the art, adjustments for degradation, systemic versus localized delivery, and rate of new protease synthesis, as well as the age, body weight, general health, sex, diet, time ,of administration, drug interaction and the severity of the condition may be necessary, and will be ascertainable with routine experimentation by those skilled in the art.

A "patient" for the purposes of the present invention includes both humans and other animals, particularly mammals, and organisms. Thus the methods are applicable to both human therapy and veterinary applications. In the preferred embodiment the patient is a mammal, and in the most preferred embodiment the patient is human.

The administration of the breast cancer proteins and modulators of the present invention can be done in a variety of ways as discussed above, including, but not limited to, orally, subcutaneously, intravenously, intranasally, transdermally, intraperitoneally, intramuscularly, intrapulmonary, vaginally, rectally, or intreocularly. In some instances, for example, in the treatment of wounds and inflammation, the breast cancer proteins and modulators may be directly applied as a solution or spray.

The pharmaceutical compositions of the present invention comprise a breast cancer protein in a form suitable for administration to a patient in the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandellc acid, methanesulfonic acid, ethanesulfonic acid, p-toluenesulfonic acid, salicylic acid and the like. "Pharmaceutcally acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, trietlylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

In a preferred embodiment, breast cancer proteins and modulators are administered as therapeutic agents, and can be formulated as outlined above. Similarly, breast cancer genes (including both the full-length sequence, partial sequences, or regulatory sequences of the breast cancer coding regions) can be administered in gene therapy applications, as is known in the art. These breast cancer genes can include antisense applications, either as gene therapy (i.e. for incorporation into the genome) or as antisense compositions, as will be appreciated by those in the art.

In a preferred embodiment, breast cancer genes are administered as DNA vaccines, either single genes or combinations of breast cancer genes. Naked DNA vaccines are generally known in the art. Brower, Nature Biotechnology, 16:1304–1305 (1998).

In one embodiment, breast cancer genes of the present invention are used as DNA vaccines. Methods for the use of genes as DNA vaccines are well known to one of ordinary skill in the art, and include placing a breast cancer gene or portion of a breast cancer gene under the control of a promoter for expression in a patient with breast cancer. The breast cancer gene used for DNA vaccines can encode full-length breast cancer proteins, but more preferably encodes portions of the breast cancer proteins including peptides derived from the breast cancer protein. In a preferred embodiment a patient is immunized with a DNA vaccine comprising a plurality of nucleotide sequences derived from a breast cancer gene. Similarly, it is possible to immunize a patient with a plurality of breast cancer genes or portions thereof as defined herein. Without being bound by theory, expression of the polypeptide encoded by the DNA vaccine, cytotoxic T-cells, helper T-cells and antibodies are induced which recognize and destroy or eliminate cells expressing breast cancer proteins.

In a preferred embodiment, the DNA vaccines include a gene encoding an adjuvant molecule with the DNA vaccine. Such adjuvant molecules include cytokines that increase the immunogenic response to the breast cancer polypeptide encoded by the DNA vaccine. Additional or alternative adjuvants are known to those of ordinary skill in the art and find use in the invention.

In another preferred embodiment breast cancer genes find use in generating animal models of breast cancer. For example, as is appreciated by one of ordinary skill in the art, when the breast cancer gene identified is repressed or diminished in breast cancer tissue, gene therapy technology wherein antisense RNA directed to the breast cancer gene will also diminish or repress expression of the gene. An animal generated as such serves as an animal model of breast cancer that finds use in screening bioactive drug candidates. Similarly, gene knockout technology, for example as a result of homologous recombination with an appropriate gene targeting vector, will result in the absence of the breast cancer protein. When desired, tissue-specific expression or knockout of the breast cancer protein may be necessary.

It is also possible that the breast cancer protein is overexpresed in breast cancer. As such, transgenic animals can be generated that overexpress the breast cancer protein. Depending on the desired expression level, promoters of various strengths can be employed to express the transgene. Also, the number of copies of the integrated transgene can be determined and compared for a determination of the expression level of the transgene. Animals generated by such methods find use as animal models of breast cancer and are additionally useful in screening for bioactive molecules to treat disorders related to the breast cancer protein.

It is understood that the examples described herein in no way serve to limit the true scope of this invention, but rather are presented for illustrative purposes. All references and sequences of accession numbers cited herein are incorporated by reference in their entirety.

EXAMPLES

Example 1

Tissue Preparation, Labeling Chips, and Fingerprints

Purify Total RNA From Tissue Using TRizol Reagent

Estimate tissue weight. Homogenize tissue samples in 1 ml of TRizol per 50 mg of tissue using a Polytron 3100 homogenizer. The generator/probe used depends upon the tissue size. A generator that is too large for the amount of tissue to be homogenized will cause a loss of sample and lower RNA yield. Use the 20 mm generator for tissue weighing more than 0.6 g. If the working volume is greater than 2 ml, then homogenize tissue in a 15 ml polypropylene tube (Falcon 2059). Fill tube no greater than 10 ml.

Homogenization

Before using generator, it should have been cleaned after last usage by running it through soapy H20 and rinsing thoroughly. Run through with EtOH to sterilize. Keep tissue frozen until ready. Add TRizol directly to frozen tissue then homogenize.

Following homogenization, remove insoluble material from the homogenate by centrifugation at 7500×g for 15 min. In a Sorvall superspeed or 12,000×g for 10 min. in an Eppendorf centrifuge at 4° C. Transfer the cleared homogenate to a new tube(s). The samples may be frozen now at −60 to −70° C. (and kept for at least one month) or you may continue with the purification.

Phase Separation

Incubate the homogenized samples for 5 minutes at room temperature. Add 0.2 ml of chloroform per 1 ml of TRizol reagent used in the original homogenization. Cap tubes securely and shake tubes vigorously by hand (do not vortex) for 15 seconds. Incubate samples at room temp. for 2–3 minutes. Centrifuge samples at 6500 rpm in a Sorvall superspeed for 30 min. at 4° C. (You may spin at up to 12,000×g for 10 min. but you risk breaking your tubes in the centrifuge.)

RNA Precipitation

Transfer the aqueous phase to a fresh tube. Save the organic phase if isolation of DNA or protein is desired. Add 0.5 ml of isopropyl alcohol per 1 ml of TRizol reagent used in the original homogenization. Cap tubes securely and invert to mix. Incubate samples at room temp. for 10 minutes. Centrifuge samples at 6500 rpm in Sorvall for 20 min at 4° C.

RNA Wash

Pour off the supernate. Wash pellet with cold 75% ethanol. Use 1 ml of 75% ethanol per 1 ml of TRizol reagent used in the initial homogenization. Cap tubes securely and invert several times to loosen pellet (Do not vortex). Centrifuge at <8000 rpm (<7500×g) for 5 minutes at 4° C. Pour off the wash. Carefully transfer pellet to an eppendorf tube (let it slide down the tube into the new tube and use a pipet tip to help guide it in if necessary). Depending on the volumes you are working with, you can decide what size tube(s) you want to precipitate the RNA in. When I tried leaving the RNA in the large 15 ml tube, it took so long to dry (i.e. it did not dry) that I eventually had to transfer it to a smaller tube. Let pellet dry in hood. Resuspend RNA in an appropriate volume of DEPC H$_2$O. Try for 2–5 ug/ul. Take absorbance readings.

Purify Poly A+ mRNA From Total RNA or Clean Up Total RNA With Qiagen's RNeasy Kit Purification of poly A$^+$ mRNA from total RNA Heat oligotex suspension to 37° C. and mix immediately before adding to RNA. Incubate Elution Buffer at 70° C. Warm up 2× Binding Buffer at 65° C. if there is precipitate in the buffer. Mix total RNA with DEPC-treated water, 2× Binding Buffer, and Oligotex according to Table 2 on page 16 of the Oligotex Handbook. Incubate for 3 minutes at 65° C. Incubate for 10 minutes at room temperature.

Centrifuge for 2 minutes at 14,000 to 18,000 g. If centrifuge has a "soft setting," then use it. Remove supernatant without disturbing Oligotex pellet. A little bit of solution can be left behind to reduce the loss of Oligotex. Save sup until certain that satisfactory binding and elution of poly A+ mRNA has occurred.

Gently resuspend in Wash Buffer OW2 and pipet onto spin column. Centrifuge the spin column at full speed (soft setting if possible) for 1 minute.

Transfer spin column to a new collection tube and gently resuspend in Wash Buffer OW2 and centrifuge as describe herein.

Transfer spin column to a new tube and elute with 20 to 100 ul of preheated (70° C.) Elution Buffer. Gently resuspend Oligotex resin by pipetting up and down. Centrifuge as above. Repeat elution with fresh elution buffer or use first eluate to keep the elution volume low.

Read absorbance, using diluted Elution Buffer as the blank.

Before proceeding with cDNA synthesis, the mRNA must be precipitated. Some component leftover or in the Elution Buffer from the Oligotex purification procedure will inhibit downstream enzymatic reactions of the mRNA.

Ethanol Precipitation

Add 0.4 vol. of 7.5M $NH_4OAc$+2.5 vol. of cold 100% ethanol. Precipitate at −20° C. 1 hour to overnight (or 20–30 min. at −70° C.). Centrifuge at 14,000–16,000×g for 30 minutes at 4° C. Wash pellet with 0.5 ml of 80% ethanol (−20° C.) then centrifuge at 14,000–16,000×g for 5 minutes at room temperature. Repeat 80% ethanol wash. Dry the last bit of ethanol from the pellet in the hood. (Do not speed vacuum). Suspend pellet in DEPC $H_2O$ at 1 ug/ul concentration.

Clean Up Total RNA Using Qiagen's RNeasy Kit

Add no more than 100 ug to an RNeasy column. Adjust sample to a volume of 100 ul with RNase-free water. Add 350 ul Buffer RLT then 250 ul ethanol (100%) to the sample. Mix by pipetting (do not centrifuge) then apply sample to an RNeasy mini spin column. Centrifuge for 15 sec at >10,000 rpm. If concerned about yield, re-apply flowthrough,to column and centrifuge again. Transfer column to a new 2-ml collection tube. Add 500 ul Buffer RPE and centrifuge for 15 sec at >10,000 rpm. Discard flowthrough. Add 500 ul Buffer RPE and centrifuge for 15 sec at >10,000 rpm. Discard flowthrough then centrifuge for 2 min at maximum speed to dry column membrane. Transfer column to a new 1.5-ml collection tube and apply 30–50 ul of RNase-free water directly onto column membrane. Centrifuge 1 min at >10, 000 rpm. Repeat elution. Take absorbance reading. If necessary, ethanol precipitate with ammonium acetate and 2.5×volume 100% ethanol.

Make cDNA Using Gibco's "SuperScript Choice System for cDNA Synthesis" Kit First Strand cDNA Synthesis Use 5 ug of total RNA or 1 ug of polyA+ mRNA as staring material. For total RNA, use 2 ul of SuperScript RT. For polyA+ mRNA, use 1 ul of SuperScript RT. Final volume of first strand synthesis mix is 20 ul. RNA must be in a volume no greater than 10 ul. Incubate RNA with 1 ul of 100 pmol T7–T24 oligo for 10 min at 70C. On ice, add 7 ul of: 4 ul 5×1$^{st}$ Strand Buffer, 2 ul of 0.1M DTT, and 1 ul of 10 mM dNTP mix. Incubate at 37C for 2 min then add SuperScript RT incubate at 37C for 1 hour.

Second Strand Synthesis

Place 1$^{st}$ strand reactions on ice.

Add: 91 ul DEPC H20
   30 ul 5×2$^{nd}$ Stand Buffer
   3 ul 10 mM dNTP mix
   1 ul 10 U/ul *E.coli* DNA Ligase
   4 ul 10 U/ul *E.coli* DNA Polymerase
   1 ul 2 U/ul RNase H Make the above into a mix if there are more than 2 samples, Mix and incubate 2 hours at 16C. Add 2 ul T4 DNA Polymerase. Incubate 5 min at 16C. Add 10 ul of 0.5M EDTA Clean Up cDNA Phenol:Chloroform:Isoamyl Alcohol (25:24:1) purification using Phase-Lock gel tubes:

Centrifuge PLG tubes for 30 sec at maximum speed. Transfer cDNA mix to PLG tube. Add equal volume of phenol:chloroform:isamyl alcohol and shake vigorously (do not vortex). Centrifuge 5 minutes at maximum speed. Transfer top aqueous solution to a new tube. Ethanol precipitate: add 7.5×5M NH4Oac and 2.5× volume of 100% ethanol. Centrifuge immediately at room temp. for 20 min, maximum speed. Remove sup then wash pellet 2× with cold 80% ethanol. Remove as much ethanol wash as possible then let pellet air dry. Resuspend pellet in 3 ul RNase free water.

In Vitro Transcription (IVT) and Labeling With Biotin

Pipet 1.5 ul of cDNA into a thin-wall PCR tube.

Make NTP Labeling Mix:

Combine at room temperature: 2 ul T7 10×ATP (75 mM) (Ambion)
   2 ul T7 10×GTP (75 mM) (Ambion)
   1.5 ul T7 10×CTP (75 mM) (Ambion)
   1.5 ul T7 10×UTP (75 mM) (Ambion)
   3.75 ul 10 mM Bio-11-UTP (Boehringer-Mannheim/ Roche or Enzo)
   3.75 ul 10 mM Bio-16-CTP (Enzo)
   2 ul 10× T7 transcription buffer (Ambion)
   2 ul 10× T7 enzyme mix (Ambion)

Final volume of total reaction is 20 ul. Incubate 6 hours at 37C in a PCR machine.

RNeasy Clean-up of IVT Product

Follow previous instructions for RNeasy columns or refer to Qiagen's RNeasy protocol handbook.

cRNA will most likely need to be ethanol precipitated. Resuspend in a volume compatible with the fragmentation step.

Fragmentation 15 ug of labeled RNA is usually fragmented. Try to minimize the fragmentation reaction volume; a 10 ul volume is recommended but 20 ul is all right. Do not go higher than 20 ul because the magnesium in the fragmentation buffer contributes to precipitation in the hybridization buffer. Fragment RNA by incubation at 94C for 35 minutes in 1×Fragmentation buffer.

5×Fragmentation buffer:

200 mM Tris-acetate, pH 8.1
   500 mM KOAc
   150 mM MgOAc

The labeled RNA transcript can be analyzed before and after fragmentation. Samples can be heated to 65C for 15 minutes and electrophoresed on 1% agarose/TBE gels to get an approximate idea of the transcript size range Hybridization 200 ul (10 ug cRNA) of a hybridization mix is put on the chip. If multiple hybridizations are to be done (such as cycling through a 5 chip set), then it is recommended that an initial hybridization mix of 300 ul or more be made.

Hybridization Mix: fragment labeled RNA (50 ng/ul final conc.)

50 pM 948-b control oligo 1.5 pM BioB 5 pM BioC 25 pM BioD 100 pM CRE 0.1 mg/ml herring sperm DNA 0.5 mg/ml acetyiated BSA to 300 ul with 1×MES hyb. buffer The instruction manuals for the prods used herein are incorporated herein in their entirety.

| Labelling Protocol Provided Herein |
| --- |
| Hybridization reaction: |
| Start with non-biotinylated IVT (purified by RNeasy columns) |
| (see example 1 for steps from tissue to IVT) |
| IVT antisense RNA; 4 vg: $\mu l$ |
| Random Hexamers (1 $\mu g/\mu l$): 4 $\mu l$ |
| H$_2$O: $\mu l$ |
| 14 $\mu l$ |

Incubate 70° C., 10 min. Put on ice.

| Reverse transcription: | |
| --- | --- |
| 5X First Strand (BRL) buffer: | 6 $\mu l$ |
| 0.1 M DTT: | 3 $\mu l$ |
| 50X dNTP mix: | 0.6 $\mu l$ |
| H2O: | 2.4 $\mu l$ |
| Cy3 or Cy5 dUTP (1 mM): | 3 $\mu l$ |
| SS RT II (BRL): | 1 $\mu l$ |
| | 16 $\mu l$ |

Add to hybridization reaction.

Incubate 30 min., 42° C.

Add 1 $\mu l$ SSll and let go for another hour. Put on ice.

SOX dNTP mix (25 mM of cold dATP, dCTP, and dGTP, 10mM of dTTP: 25 $\mu l$ each of 100 mM dATP, dCTP, and dGTP; 10 $\mu l$ of 100 mM dTTP to 15 $\mu l$ H2O. dNTPs from Pharmacia)

| RNA degradation: | |
| --- | --- |
| | 86 $\mu l$ H$_2$O |
| Add 1.5 $\mu l$ 1M NaOH/2 mM EDTA, | 10 $\mu l$ 10N NaOH |
| incubate at 65° C., 10 min. | 4 $\mu l$ 50 mM EDTA |

U-Con 30

500 $\mu l$ TE/sample spin at 7000 g for 10 min, save flow through for purification Qiagen Purification suspend u-con recovered material in 500 $\mu l$ buffer PB proceed w/normal Qiagen protocol DNAse digest Add 1 $\mu l$ of 1/100 dil of DNAse/30 $\mu l$ Rx and incubate at 37° C. for 15 min.

5 min 95° C. to denature enzyme

| Sample | |
| --- | --- |
| Add: | |
| Cot-1 DNA: | 10 $\mu l$ |
| 50X dNTPs: | 1 $\mu l$ |
| 20X SSC: | 2.3 $\mu l$ |
| Na pyro phosphate: | 7.5 $\mu l$ |
| 10 mg/ml Herring sperm DNA | 1 $\mu l$ of 1/10 dilution |
| | 21.8 final vol. |

Dry down in speed vac.

Resuspend in 15 $\mu l$ H$_2$O.

Add 0.38 $\mu l$ 10% SDS.

Heat 95° C., 2 min.

Slow cool at room temp. for 20 min.

Put on slide and hybridize overnight at 64° C.

| Washing after the hybridization: | |
| --- | --- |
| 3X SSC/0.03% SDS: | 2 min. 37.5 mls 20X SSC + 0.75 mls 10% SDS in 250 mls H$_2$O |
| 1X SSC: 5 min. | 12.5 mls 20X SSC in 250 mls H$_2$O |
| 0.2X SSC: 5 min. | 2.5 mls 20X SSC in 250 mls H$_2$O |

Dry slides in centrifuge, 1000 RPM, 1 min. Scan using a Photomultiplier tube at appropriate fluorescent channels.

EXAMPLE 2

Expression Profile of BFA4

The level of BFA4 was assayed in a variety of breast cancer, colon cancer and normal tissues. cDNA was prepared and placed on a chip as described in Example 1. Expression of BFA4 was determined using Affymetrix GensChip™ expression arrays (Santa Clara, Calif.) according to the manufacturer's protocol.

As shown in FIG. 3, BFA4 is upregulated in a large number of breast cancer tissues.

What is claimed is:

1. A method for determining the presence or absence of a breast cancer cell in a patient, the method comprising:
   (i) detecting a nucleic acid encoding SEQ ID NO:2 in a sample from the patient, and
   (ii) comparing expression levels of the nucleic acid in the sample from the patient to expression levels of the nucleic acid in a normal tissue sample;
   wherein an increase in expression of the nucleic acid in the sample from the patient as compared to the normal tissue sample indicates the presence of a breast cancer cell in the patient.

2. The method of claim 1, wherein the sample from the patient comprises isolated nucleic acids.

3. The method of claim 2, wherein the nucleic acids are mRNA.

4. The method of claim 1, wherein the sample from the patient is breast tissue.

5. The method of claim 1, wherein the nucleic acid comprises SEQ ID NO:1.

6. The method of claim 1, wherein said detecting is carried out by using a labeled nucleic acid probe.

7. The method of claim 1, wherein said detecting is carried out by utilizing a biochip comprising a nucleic acid sequence encoding SEQ ID NO: 2, wherein said nucleic acid sequence is at least 90% identical to SEQ ID NO: 1.

8. The method of claim 1, wherein the nucleic acid encoding SEQ ID NO: 2 is at least 95% identical to SEQ ID NO: 1.

* * * * *